United States Patent
Wheatley et al.

(10) Patent No.: US 9,220,709 B2
(45) Date of Patent: Dec. 29, 2015

(54) DRUG LOADED CONTRAST AGENTS: COMBINING DIAGNOSIS AND THERAPY

(75) Inventors: Margaret A. Wheatley, Media, PA (US); Odelia Mualem Burstein, Philadelphia, PA (US); John R. Eisenbrey, Middletown, DE (US); Dalia El-Sherif, King of Prussia, PA (US)

(73) Assignee: Drexel University, Philadelphia, PA (US)

( * ) Notice: Subject to any disclaimer, the term of this patent is extended or adjusted under 35 U.S.C. 154(b) by 1552 days.

(21) Appl. No.: 12/301,423

(22) PCT Filed: May 21, 2007

(86) PCT No.: PCT/US2007/069393
§ 371 (c)(1),
(2), (4) Date: Nov. 18, 2008

(87) PCT Pub. No.: WO2007/137236
PCT Pub. Date: Nov. 29, 2007

(65) Prior Publication Data
US 2009/0196827 A1    Aug. 6, 2009

Related U.S. Application Data

(60) Provisional application No. 60/802,204, filed on May 19, 2006.

(51) Int. Cl.
| A61K 9/51 | (2006.01) |
| A61K 31/704 | (2006.01) |
| A61K 31/405 | (2006.01) |
| A61K 9/00 | (2006.01) |
| A61K 9/16 | (2006.01) |
| A61K 41/00 | (2006.01) |
(Continued)

(52) U.S. Cl.
CPC ............ *A61K 31/405* (2013.01); *A61K 9/0009* (2013.01); *A61K 9/1647* (2013.01); *A61K 9/5153* (2013.01); *A61K 9/5192* (2013.01); *A61K 41/0028* (2013.01); *A61K 47/48238* (2013.01); *A61K 47/48869* (2013.01); *A61K 49/225* (2013.01); *A61K 9/1694* (2013.01)

(58) Field of Classification Search
CPC ... A61K 31/00; A61K 9/1647; A61K 9/5192; A61K 49/225; A61K 9/141; A61K 9/50; A61K 9/5031; A61K 9/5021; A61K 9/513; B01J 13/12; B82Y 5/00
See application file for complete search history.

(56) References Cited

U.S. PATENT DOCUMENTS

| 5,352,436 A | 10/1994 | Wheatley |
| 5,585,112 A | 12/1996 | Unger |

(Continued)

FOREIGN PATENT DOCUMENTS

| WO | WO94/21301 | 9/1994 |
| WO | WO98/47540 | 10/1998 |
| WO | WO02/078611 | 10/2002 |

*Primary Examiner* — Lakshmi Channavajjala
(74) *Attorney, Agent, or Firm* — Saul Ewing LLP; Kathryn Doyle; Brian R. Landry

(57) ABSTRACT

This invention provides an improvement to methods of drug loading of ultrasound contrast agents. Echogenic drug-loaded polymer microcapsules, nanocapsules, or mixtures thereof produced by the method of the invention wherein the echogenic drug-loaded polymer microcapsules, nanocapsules, or mixtures thereof contain at least 10% more of a drug as compared to (1) echogenic drug-loaded polymer microcapsules, nanocapsules, or mixtures thereof prepared by adding drug prior to emulsifying or (2) echogenic drug-loaded polymer microcapsules, nanocapsules, or mixtures thereof prepared by adding drug to lyophilized polymer microcapsules, nanocapsules, or mixtures thereof.

13 Claims, 7 Drawing Sheets

(51) Int. Cl.
*A61K 47/48* (2006.01)
*A61K 49/22* (2006.01)

(56) References Cited

U.S. PATENT DOCUMENTS

| | | |
|---|---|---|
| 5,614,169 A | 3/1997 | Klaveness |
| 5,637,289 A | 6/1997 | Klaveness |
| 5,648,062 A | 7/1997 | Klaveness |
| 5,648,095 A | 7/1997 | Illum |
| 5,827,502 A | 10/1998 | Klaveness |
| 5,955,143 A | 9/1999 | Wheatley |
| 2002/0159952 A1* | 10/2002 | Unger ............ 424/9.51 |
| 2004/0161384 A1* | 8/2004 | Wheatley et al. ...... 424/9.5 |

* cited by examiner

DRUG LOADED CONTRAST AGENTS: COMBINING DIAGNOSIS AND THERAPY

CROSS-REFERENCE TO RELATED APPLICATIONS

This application is the U.S. national phase application filed under 35 U.S.C. §371 claiming benefit to International Patent Application No. PCT/US2007/069393, filed on May 21, 2007 and U.S. Provisional Patent Application No. 60/802,204, filed on May 19, 2006, which is entitled to priority under 35 U.S.C. §119(a) each of which application is hereby incorporated herein by reference in its entirety.

STATEMENT REGARDING FEDERALLY SPONSORED RESEARCH OR DEVELOPMENT

This research was supported in part by the U.S. Government funds (NIH grant numbers CA 102238 and HL 52901) and the U.S. Government therefore has certain rights in the invention.

BACKGROUND OF THE INVENTION

1. Field of Invention

This invention relates to novel methods of drug loading of ultrasound contrast agents.

2. Description of Related Art

Ultrasound contrast agents are used routinely in medical diagnostic, as well as industrial, ultrasound. For medical diagnostic purposes, contrast agents are usually gas bubbles, which derive their contrast properties from the large acoustic impedance mismatch between blood and the gas contained therein. Important parameters for the contrast agent include particle size, imaging frequency, density, compressibility, particle behavior (surface tension, internal pressure, bubble-like qualities), biodistribution and tolerance.

Gas-filled particles are by far the best reflectors. Various bubble-based suspensions with diameters in the 1 to 15 micron range have been developed for use as ultrasound contrast agents. Bubbles of these dimensions have resonance frequencies in the diagnostic ultrasonic range, thus improving their backscatter enhancement capabilities. Sonication has been found to be a reliable and reproducible technique for preparing standardized echo contrast agent solutions containing uniformly small microbubbles. Bubbles generated with this technique typically range in size from 1 to 15 microns in diameter with a mean bubble diameter of 6 microns (Keller et al. 1986. J. Ultrasound Med. 5:493-498). However, the durability of these bubbles in the blood stream has been found to be limited and research continues into new methods for production of microbubbles. Research has also focused on production of hollow microparticles for use as contrast agents wherein the microparticle can be filled with gas and used in ultrasound imaging. These hollow microparticles, however, also have uses as drug delivery agents when associated with drug products. These hollow microparticles can also be associated with an agent which targets selected cells and/or tissues to produce targeted contrast agents and/or targeted drug delivery agents. Surfactant stabilized microbubble mixtures for use as ultrasound contrast agents are disclosed in U.S. Pat. No. 5,352,436. Liposome encapsulation of therapeutical agents is described in U.S. Pat. No. 5,585,112 to Unger et al.

WO 98/47540 discloses a contrast agent for diagnostic ultrasound and targeted disease imaging and drug delivery comprising a dispersion of a biocompatible azeotropic mixture, which contains a halocarbon.

WO 94/21301 discloses an ultrasound agent consisting of a biocompatible oil-in-water emulsion in which the oil phase comprises an oil-soluble gas/fluid or gas precursor.

U.S. Pat. No. 5,637,289, U.S. Pat. No. 5,648,062, U.S. Pat. No. 5,827,502 and U.S. Pat. No. 5,614,169 disclose contrast agents comprising water-soluble, microbubble generating carbohydrate microparticles, admixed with at least 20% of a non-surface active, less water-soluble material, a surfactant or an amphiphilic organic acid. The agent is prepared by dry mixing, or by mixing solutions of components followed by evaporation and micronizing.

U.S. Pat. No. 5,648,095 discloses hollow microcapsules for use in imaging and drug delivery. The hollow microcapsules are made by combining a volatile oil with an aqueous phase including a water soluble material such as starch or a polyethylene glycol conjugate to form a primary emulsion. The primary emulsion then is combined with a second oil to form a secondary emulsion, which is hardened and allows for microcapsules to form around a liquid core of the volatile oil. The volatile oil is then removed by evaporation leaving a hollow microcapsule.

U.S. Pat. No. 5,955,143 discloses hollow polymer microcapsules that are produced by dissolving a film-forming polymer in a volatile non-aqueous solvent, dispersing into the polymer solution finely divided particles of a volatilizable solid core material, inducing formation of a solid polymer coating on the particulate solid core material to produce polymer microcapsules having an encapsulated solid core. This core is then removed to result in hollow microcapsules that can be then filled with gas for contrast imaging.

There remains a need for methods of production of biocompatible, biodegradable echogenic microcapsules and nanocapsules of a reproducible size range that can be used for contrast imaging and/or drug delivery with or without targeting which have high loading capabilities and acceptable echogenicity.

SUMMARY OF THE INVENTION

The improved methods of drug adsorption allow for production of ultrasound contrast agent with acceptable echogenicity for imaging purposes and unexpectedly high drug loading capability and an ability to regulate stability by selecting components such as polymer type.

In one aspect, the invention is a hardening stage adsorption method for producing echogenic drug-loaded polymer microcapsules, nanocapsules, or mixtures thereof, which comprises the following steps:

(a) forming a first mixture comprising a solution of at least one polymer in at least one volatile non-polar solvent and optionally at least one non-water soluble sublimable substance;

(b) forming a second mixture comprising a solution of at least one water soluble sublimable substance in at least one polar solvent;

(d) adding said first mixture to said second mixture to form a third mixture;

(e) emulsifying the third mixture to produce a first population of said polymer microcapsules, nanocapsules, or mixtures thereof comprising said at least one polymer, said at least one water-soluble sublimable substance, and optionally, said at least one non-water sublimable soluble substance;

(f) mixing said first population of polymer microcapsules, nanocapsules, or mixtures thereof with a surfactant solution and homogenizing to break apart said first population of microcapsules or nanocapsules to form a second population of polymer microcapsules, nanocapsules, or mixtures thereof that are smaller in size then said first population;

(g) hardening said second population of polymer microcapsules, nanocapsules, or mixtures thereof by contacting with at least one hardening solvent comprising a drug which is dissolved or dispersed in said at least one hardening solvent to form a first population of drug-loaded polymer microcapsules, nanocapsules, or mixtures thereof in which at least 95% of the non polar solvent is removed;

(h) optionally removing traces of said at least one hardening solvent and thereby further hardening said first population of drug-loaded polymer microcapsules, nanocapsules, or mixtures thereof; and (i) removing said water soluble sublimable substance and said non water soluble sublimable substance if present from said drug-loaded population of polymer microcapsules, nanocapsules, or mixtures thereof to form echogenic drug-loaded polymer microcapsules, nanocapsules, or mixtures thereof which comprise at least 10% more of said drug as compared to (1) echogenic drug-loaded polymer microcapsules, nanocapsules, or mixtures thereof prepared by adding said drug prior to said emulsifying or (2) echogenic drug-loaded polymer microcapsules, nanocapsules, or mixtures thereof prepared by adding said drug to lyophilized polymer microcapsules, nanocapsules, or mixtures thereof.

In another aspect, the invention is a pre-hardening stage adsorption method for producing echogenic drug-loaded polymer microcapsules, nanocapsules, or mixtures thereof which comprises the following steps:

(a) forming a first mixture comprising a solution of at least one polymer in at least one volatile non-polar solvent and optionally at least one non-water soluble sublimable substance;

(b) forming a second mixture comprising a solution of at least one water soluble sublimable substance in at least one polar solvent;

(c) adding said first mixture to said second mixture to form a third mixture;

(d) emulsifying the third mixture to produce a first population of polymer microcapsules, nanocapsules, or mixtures thereof comprising said at least one polymer, said at least one water-soluble sublimable substance, and optionally, said at least one non-water sublimable soluble substance;

(e) mixing said first population of polymer microcapsules, nanocapsules, or mixtures thereof with a surfactant solution and homogenizing to break apart said first population of polymer microcapsules, nanocapsules, or mixtures thereof to form a second population of polymer microcapsules, nanocapsules, or mixtures thereof that are smaller in size then said first population;

(f) mixing said first population of polymer microcapsules, nanocapsules, or mixtures thereof with a surfactant solution and homogenizing to break apart said first population of polymer microcapsules, nanocapsules, or mixtures thereof to form a second population of polymer microcapsules, nanocapsules, or mixtures thereof that are smaller in size then said first population;

(g) contacting said second population of polymer microcapsules, nanocapsules, or mixtures thereof with a solution of a drug in a non-solvent for said polymer and thereby adsorbing at least a portion of said drug at least onto the surface of said second population of polymer microcapsules, nanocapsules, or mixtures thereof;

(h) removing said non-solvent having less of said drug due to said adsorbing at least a portion of said drug;

(i) hardening said second population of polymer microcapsules, nanocapsules, or mixtures thereof having adsorbed at least a portion of said drug by contacting with at least one hardening solvent to form a population of drug-loaded polymer microcapsules, nanocapsules, or mixtures thereof in which at least 95% of the non polar solvent is removed;

(j) optionally removing traces of said hardening solvent and thereby further hardening said population of drug-loaded polymer microcapsules, nanocapsules, or mixtures thereof; and (k) removing said water soluble sublimable substance and said non water soluble sublimable substance if present from said drug-loaded population of polymer microcapsules, nanocapsules, or mixtures thereof to form echogenic drug-loaded polymeric microcapsules or nanocapsules which comprise at least 10% more of said drug as compared to (1) echogenic drug-loaded polymer microcapsules, nanocapsules, or mixtures thereof prepared by adding said drug prior to said emulsifying or (2) echogenic drug-loaded polymer microcapsules, nanocapsules, or mixtures thereof prepared by adding said drug to lyophilized polymer microcapsules, nanocapsules, or mixtures thereof.

In a preferred embodiment of the above aspects, step (f) further includes adding an extraction solvent and stirring to begin removal of the non-polar solvent.

In certain embodiments of the above aspects, removing of said water soluble sublimable substance and the non water soluble sublimable substance if present is achieved by freeze drying.

In certain embodiments of the above aspects, removing of at least one hardening solvent in step (h) is done by washing said first population of drug-loaded polymer microcapsules, nanocapsules, or mixtures thereof with a fresh portion of at least one hardening solvent optionally comprising said drug followed by washing with water or buffer.

In certain embodiments of the above aspects, drug is added to at least one fresh portion of hardening solvent in step (h).

In certain embodiments of the above aspects, in step (a), at least one non water soluble sublimable substance is dissolved in at least one volatile non-polar solvent.

In certain embodiments of the above aspects, removing of water soluble sublimable substance and non water soluble sublimable substance is achieved by freeze drying.

In certain embodiments of the above aspects, removing of at least one hardening solvent in step (h) is done by washing first population of drug-loaded polymer microcapsules, nanocapsules, or mixtures thereof with at least one hardening solvent.

In certain embodiments of the above aspects, drug is at least one of fluorouracil, bromopyruvate, doxorubicin, and paclitaxol.

In another aspect, the invention is a hardening stage adsorption method for producing echogenic drug-loaded polymer microcapsules, nanocapsules, or mixtures thereof which comprises the following steps:

(a) forming a first mixture comprising a solution of at least one polymer in at least one volatile non-polar solvent and optionally at least one non-water soluble sublimable substance;

(b) adding at least one polar solvent to said first mixture to form a pre-emulsion;

(c) emulsifying the pre-emulsion to produce a first population of polymer microcapsules, nanocapsules, or mixtures thereof comprising said at least one polymer and said at least one non-water sublimable soluble substance;

(d) mixing said first population of polymer microcapsules, nanocapsules, or mixtures thereof with a surfactant solution and homogenizing to break apart said first population of polymer microcapsules, nanocapsules, or mixtures thereof to form a second population of polymer microcapsules, nanocapsules, or mixtures thereof that are smaller in size then said first population;

(e) hardening said second population of polymer microcapsules, nanocapsules, or mixtures thereof by contacting with at least one hardening solvent comprising a drug which is dissolved or dispersed in said at least one hardening solvent to form a first population of drug-loaded polymer microcapsules, nanocapsules, or mixtures thereof in which at least 95% of the non polar solvent is removed;

(f) optionally removing traces of said hardening solvent and thereby further hardening said first population of drug-loaded polymer microcapsules, nanocapsules, or mixtures thereof; and (g) removing said non water soluble sublimable substance from said drug-loaded population of polymer microcapsules, nanocapsules, or mixtures thereof to form echogenic drug-loaded polymer microcapsules, nanocapsules, or mixtures thereof which comprise at least 10% more of said drug as compared to (1) echogenic drug-loaded polymer microcapsules, nanocapsules, or mixtures thereof prepared by adding said drug prior to said emulsifying or (2) echogenic drug-loaded polymer microcapsules, nanocapsules, or mixtures thereof prepared by adding said drug to lyophilized polymer microcapsules, nanocapsules, or mixtures thereof.

In another aspect, the invention is a pre-hardening stage adsorption method for producing echogenic drug-loaded polymer microcapsules, nanocapsules, or mixtures thereof which comprises the following steps:

(a) forming a first mixture comprising a solution of at least one polymer in at least one volatile non-polar solvent and optionally at least one non-water soluble sublimable substance;

(b) adding said first mixture to at least one polar solvent to form a pre-emulsion;

(c) emulsifying the pre-emulsion to produce a first population of polymer microcapsules, nanocapsules, or mixtures thereof comprising said at least one polymer and said at least one non-water sublimable soluble substance;

(d) mixing said first population of microcapsules or nanocapsules with a surfactant solution and homogenizing to break apart said first population of polymer microcapsules, nanocapsules, or mixtures thereof to form a second population of polymer microcapsules, nanocapsules, or mixtures thereof that are smaller in size then said first population;

(e) contacting said second population of polymer microcapsules, nanocapsules, or mixtures thereof with a solution of a drug in a non-solvent for said polymer and thereby adsorbing at least a portion of said drug at least onto the surface of said second population of polymer microcapsules, nanocapsules, or mixtures thereof;

(f) removing said non-solvent having less of said drug due to said adsorbing of at least a portion of said drug;

(g) hardening said second population of polymer microcapsules, nanocapsules, or mixtures thereof having adsorbed at least a portion of said drug by contacting with at least one hardening solvent to form a population of drug-loaded polymer microcapsules, nanocapsules, or mixtures thereof in which at least 95% of the non polar solvent is removed;

(h) optionally removing traces of said hardening solvent and thereby further hardening said population of drug-loaded polymer microcapsules, nanocapsules, or mixtures thereof; and (i) removing said non water soluble sublimable substance from said drug-loaded population of polymer microcapsules, nanocapsules, or mixtures thereof to form echogenic drug-loaded polymer microcapsules, nanocapsules, or mixtures thereof which comprise at least 10% more of said drug as compared to (1) echogenic drug-loaded polymer microcapsules, nanocapsules, or mixtures thereof prepared by adding said drug prior to said emulsifying or (2) echogenic drug-loaded polymer microcapsules, nanocapsules, or mixtures thereof prepared by adding said drug to lyophilized polymer microcapsules, nanocapsules, or mixtures thereof.

In another aspect, the invention is an improvement in a method of making echogenic drug-loaded polymer microcapsules, nanocapsules, or mixtures thereof, wherein a portion of a drug is added to a water phase, an oil phase or both during formation of a population of polymer microcapsules, nanocapsules, or mixtures thereof from (i) a water/oil/water emulsion or (ii) a water/oil emulsion in the presence of a surfactant, wherein said water phase, said oil phase or both comprise a sublimable substance and wherein said oil phase comprises a polymer and a solvent, and wherein at the time said portion of said drug is being added said population of polymer microcapsules, nanocapsules, or mixtures thereof (1) is not hardened by (1) removal of a solvent or (2) liophilization, wherein the improvement comprises the following steps:

(a) hardening said population of microcapsules or nanocapsules by contacting with at least one hardening solvent comprising an additional portion of a drug which is dissolved or dispersed in said at least one hardening solvent to form a first population of drug-loaded polymer microcapsules, nanocapsules, or mixtures thereof in which at least 95% of the non polar solvent is removed;

(b) optionally removing traces of said hardening solvent and thereby further hardening said first population of drug-loaded polymer microcapsules, nanocapsules, or mixtures thereof; and (c) removing said sublimable substance from said drug-loaded population of polymer microcapsules, nanocapsules, or mixtures thereof to form echogenic drug-loaded polymer microcapsules, nanocapsules, or mixtures thereof.

In another aspect, the invention is an improvement in a method of making echogenic drug-loaded polymer microcapsules, nanocapsules, or mixtures thereof, wherein a portion of a drug is added to a water phase, an oil phase or both during formation of a population of polymer microcapsules, nanocapsules, or mixtures thereof from (i) a water/oil/water emulsion or (ii) a water/oil emulsion in the presence of a surfactant, wherein said water phase, said oil phase or both comprise a sublimable substance and wherein said oil phase comprises a polymer and a solvent, and wherein at the time said portion of said drug is being added said population of polymer microcapsules, nanocapsules, or mixtures thereof is not hardened by (1) removal of a solvent or (2) liophilization, wherein the improvement comprises the following steps:

(a) contacting said population of polymer microcapsules, nanocapsules, or mixtures thereof with a solution of a drug in a non-solvent for said polymer and thereby adsorbing at least a portion of said drug at least onto the surface of said population of polymer microcapsules, nanocapsules, or mixtures thereof;

(b) removing said non-solvent having less of said drug due to said adsorbing at least a portion of said drug;

(c) hardening said population of polymer microcapsules, nanocapsules, or mixtures thereof having adsorbed at least a portion of said drug by contacting with at least one hardening solvent to form a population of drug-loaded polymer microcapsules, nanocapsules, or mixtures thereof in which at least 95% of the non polar solvent is removed;

(d) optionally removing traces of said hardening solvent and thereby further hardening said population of drug-loaded polymer microcapsules, nanocapsules, or mixtures thereof; and (e) removing said sublimable substance from said drug-loaded population of polymer microcapsules, nanocapsules, or mixtures thereof to form echogenic drug-loaded polymer microcapsules, nanocapsules, or mixtures thereof.

In another aspect, the invention is a method of making echogenic drug-loaded polymer microcapsules, nanocapsules, or mixtures thereof, the method comprising (a) forming a population of polymer microcapsules, nanocapsules, or mixtures thereof from (i) a water/oil/water emulsion or (ii) a water/oil emulsion in the presence of a surfactant, wherein said water phase, said oil phase or both comprise a sublimable substance and wherein said oil phase comprises a polymer and a solvent for said polymer, wherein a portion of a drug is not added to said water phase, said oil phase or both during said forming of said population of polymer microcapsules, nanocapsules, or mixtures thereof and wherein said population of polymer microcapsules, nanocapsules, or mixtures thereof is dispersed in said solvent;

(b) hardening said population of polymer microcapsules, nanocapsules, or mixtures thereof by contacting with at least one hardening solvent comprising a drug which is dissolved or dispersed in said at least one hardening solvent to form a first population of drug-loaded polymer microcapsules, nanocapsules, or mixtures thereof in which at least 95% of the non polar solvent is removed;

(c) optionally removing traces of said hardening solvent and thereby further hardening said first population of drug-loaded polymer microcapsules, nanocapsules, or mixtures thereof; and (d) removing said sublimable substance from said drug-loaded population of polymer microcapsules, nanocapsules, or mixtures thereof to form echogenic drug-loaded polymer microcapsules, nanocapsules, or mixtures thereof which comprise at least 10% more of said drug as compared to (1) echogenic drug-loaded polymer microcapsules, nanocapsules, or mixtures thereof prepared by adding said drug prior to said hardening or (2) echogenic drug-loaded polymer microcapsules, nanocapsules, or mixtures thereof prepared by adding said drug to lyophilized polymer microcapsules, nanocapsules, or mixtures thereof.

In another aspect, the invention is a method of making echogenic drug-loaded polymer microcapsules, nanocapsules, or mixtures thereof which comprises the following steps:

(a) forming a population of polymer microcapsules, nanocapsules, or mixtures thereof from (i) a water/oil/water emulsion or (ii) a water/oil emulsion in the presence of a surfactant, wherein said water phase, said oil phase or both comprise a sublimable substance and wherein said oil phase comprises a polymer and a solvent for said polymer, wherein a portion of a drug is not added to said water phase, said oil phase or both during said forming of said population of polymer microcapsules, nanocapsules, or mixtures thereof and wherein said population of polymer microcapsules, nanocapsules, or mixtures thereof is dispersed in said solvent;

(b) contacting said population of polymer microcapsules, nanocapsules, or mixtures thereof dispersed in said solvent with a solution of a drug in a non-solvent for said polymer and thereby adsorbing at least a portion of said drug at least onto the surface of said population of polymer microcapsules, nanocapsules, or mixtures thereof;

(c) removing said non-solvent having less of said drug due to said adsorbing at least a portion of said drug;

(d) hardening said population of polymer microcapsules, nanocapsules, or mixtures thereof having adsorbed at least a portion of said drug by contacting with at least one hardening solvent to form a population of drug-loaded polymer microcapsules, nanocapsules, or mixtures thereof in which at least 95% of the non polar solvent is removed;

(e) optionally removing traces of said hardening solvent and thereby further hardening said population of drug-loaded polymer microcapsules, nanocapsules, or mixtures thereof; and (f) removing said sublimable substance from said drug-loaded population of polymer microcapsules, nanocapsules, or mixtures thereof to form echogenic drug-loaded polymer microcapsules, nanocapsules, or mixtures thereof which comprise at least 10% more of said drug as compared to (1) echogenic drug-loaded polymer microcapsules, nanocapsules, or mixtures thereof prepared by adding said drug prior to said emulsifying or (2) echogenic drug-loaded polymer microcapsules, nanocapsules, or mixtures thereof prepared by adding said drug to lyophilized polymer microcapsules, nanocapsules, or mixtures thereof.

In another aspect, the invention is echogenic drug-loaded polymer microcapsules, nanocapsules, or mixtures thereof produced by the method of the invention wherein the echogenic drug-loaded polymer microcapsules, nanocapsules, or mixtures thereof comprise at least 10% more of a drug as compared to (1) echogenic drug-loaded polymer microcapsules, nanocapsules, or mixtures thereof prepared by adding said drug prior to said emulsifying or (2) echogenic drug-loaded polymer microcapsules, nanocapsules, or mixtures thereof prepared by adding drug to lyophilized polymer microcapsules, nanocapsules, or mixtures thereof.

DETAILED DESCRIPTION OF THE INVENTION

Figure 1:
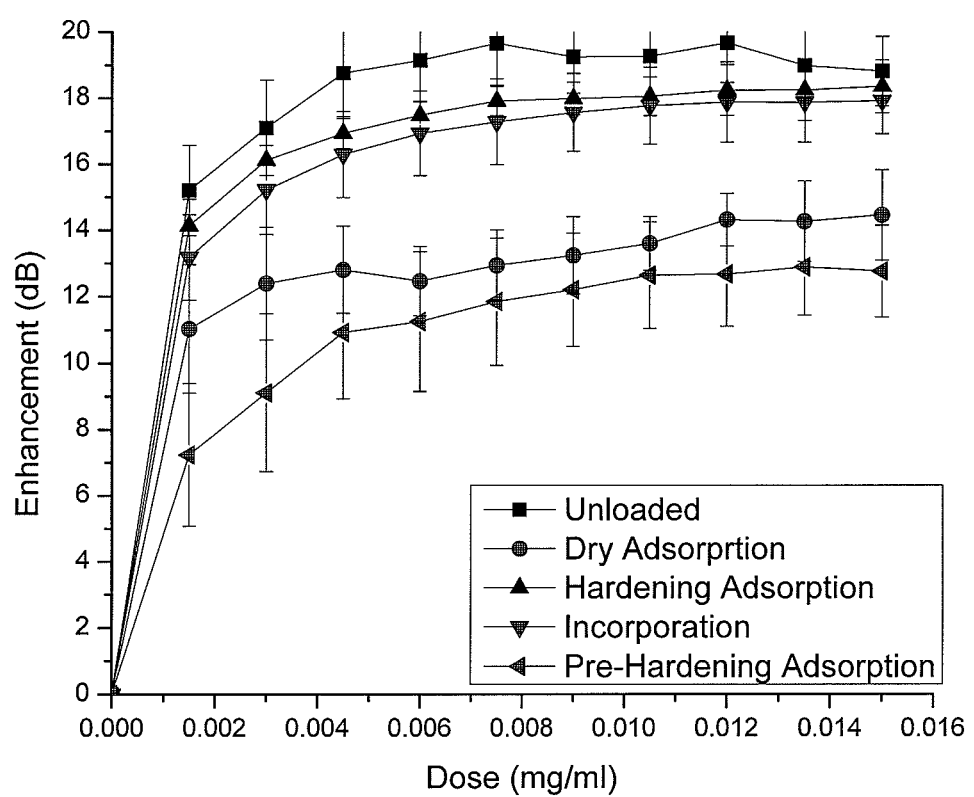
FIG. 1 demonstrates dose response curves of contrast agents loaded with a drug by different methods. Echogenic drug loaded capsules were made with camphor and ammonium carbonate as sublimable substances, PLA as a polymer, and Doxorubicin as drug.

The present invention relates to an improvement in methods of drug loading of echogenic polymer microcapsules, nanocapsules, or mixtures thereof and methods for use as contrast agents in diagnostic imaging and compositions for delivery of bioactive agents.

The present invention further relates to attachment of a targeting agent to the echogenic polymer microcapsules and nanocapsules of the contrast agents and compositions for delivery of bioactive agents of the present invention for targeted diagnostic imaging and delivery of bioactive agents to a selected tissue or tissues. Production of echogenic polymer microcapsules or nanocapsules in accordance with the present invention permits imaging and delivery of a greater load of bioactive agents. Further details on polymer microcapsules and nanocapsules can be obtained from 60/280,412, PCT/US02/10260, Ser. No. 10/472,430; EPO 02757932.5; 2002-576879 (JAP) incorporated herein in their entireties.

For purposes of the present invention, by "echogenic" it is meant that the microcapsule or nanocapsule is capable of producing a detectable echo when insonated with ultrasonic waves due to an acoustic impedance mismatch between blood and the microcapsule or nanocapsule. In a preferred embodiment, echogenic characteristics result from the microcapsule and/or nanocapsule being hollow and/or porous. By "porous" for purposes of the present invention, it is meant that the capsules contain one or more pores.

Known methods of drug loading of echogenic microcapsules or nanocapsules include the following characteristic steps:
(1) a drug is added either to organic layer or aqueous phase at the start of the double emulsion (W/O)/W method manufacture of echogenic microcapsules or nanocapsules; this method will be referred to as an "incorporation" method which is described in International Application Publication No. WO 02/078611 to Wheatley et al., incorporated herein in its entirety;
(2) echogenic microcapsules or nanocapsules are first made by a double emulsion (W/O)/W method including the lyophilization step, and then contacted with an aqueous solution of a drug. This method will be referred to as a "dry adsorption method" which is described in the International Application Publication No. WO 02/078611 to Wheatley et al.

Advantageously, the inventors discovered that the new methods can yield echogenic drug-loaded polymeric microcapsules or nanocapsules which comprise at least 10% more of drug as compared to (i) echogenic drug-loaded polymeric microcapsules or nanocapsules prepared by adding drug prior to the hardening step or (ii) echogenic drug-loaded polymeric microcapsules or nanocapsules prepared by adding drug to lyophilized polymeric microcapsules or nanocapsules. Drug payload (amount of drug per unit weight of contrast agent) is unexpectedly superior, i.e., up to 98% or greater as compared to prior art methods. Efficiency of drug addition (amount of starting drug concentration that is incorporate in the final product) is unexpectedly superior, i.e., up to 98% or greater as compared to prior art methods.

Furthermore, the methods of the invention can be used together with the prior art methods which utilize incorporating drug into a water phase or an oil phase or both prior to or at the emulsification step.

The present invention offers an improvement of previously known drug loading methods, wherein the echogenic microcapsules or nanocapsules obtained by the methods of the invention have the following characteristics:

Loss of echogenicity due to drug addition is comparable to previously known methods and acceptable for imaging needs.

Loss of echogenicity due to drug addition by hardening stage adsorption is negligible, e.g., 5%.

The stability of the agent can be informed by judicial choice of the components from which it is made, for example polymer type, which may be highly useful for triggered drug delivery.

In Tables 1 and 2, drug loading for different methods is compared.

TABLE 1

PLA: DOX Attachment to Microcapsules (DOX, mg/Polymer, g)

| % Starting Concentration (mg DOX/mg Polymer) | Loading Method: | | | |
|---|---|---|---|---|
| | Dry Adsorption | Pre-Hardening Adsorption | Hardening-stage Adsorption | Incorporation |
| 0.10% | 0.10 | 0.88 | 0.98 | 0.21 |
| 0.26% | 0.23 | Not Available | 5.72 | 0.68 |
| 0.55% | 0.49 | Not Available | 8.29 | 3.79 |
| 1.44% | 0.61 | 3.97 | 19.90 | 5.51 |
| 3.00% | 0.60 | 6.25 | 22.68 | 6.15 |
| 4.00% | 0.60 | 6.48 | 24.07 | 5.54 |

TABLE 2

PLGA: DOX Attachment to Microcapsules (DOX, mg/Polymer, g)

| % Starting Concentration (mg DOX/mg Polymer) | Loading Method: | | | |
|---|---|---|---|---|
| | Dry Adsorption | Pre-Hardening Adsorption | Hardening-stage Adsorption | Incorporation |
| 0.10% | 0.20 | 1.00 | 1.00 | 1.00 |
| 0.26% | 0.52 | Not Available | 2.60 | 2.60 |
| 0.55% | 0.72 | Not Available | 5.50 | 5.50 |
| 1.44% | 0.84 | 13.21 | 14.40 | 12.16 |
| 3.00% | 0.84 | 21.00 | 21.01 | 15.20 |
| 4.00% | 0.94 | 20.00 | 24.23 | 17.17 |

Drug loading methods of the invention will now be described in detail.

Hardening Stage Adsorption Method

In this method, the inventors have discovered that prior to lyophilization and at the hardening stage (e.g., contacting with hexane) of the capsules, the addition of a drug to a hardening solvent achieves a significantly greater load. This method is referred to herein as hardening stage adsorption, since the drug is added at the stage at which the capsules are hardened. Exemplary methods demonstrating the hardening stage adsorption is described in Examples 7, 9, 11, and 14.

Thus, in one aspect of the invention, a hardening stage adsorption method for producing echogenic drug-loaded polymer microcapsules, nanocapsules, or mixtures thereof, comprises the following steps:

(a) forming a first mixture comprising a solution of at least one polymer in at least one volatile non-polar solvent and optionally at least one non-water soluble sublimable substance;

(b) forming a second mixture comprising a solution of at least one water soluble sublimable substance in at least one polar solvent;

(d) adding said first mixture to said second mixture to form a third mixture;

(e) emulsifying the third mixture to produce a first population of said polymer microcapsules, nanocapsules, or mixtures thereof comprising said at least one polymer, said at least one water-soluble sublimable substance, and optionally, said at least one non-water sublimable soluble substance;

(f) mixing said first population of polymer microcapsules, nanocapsules, or mixtures thereof with a surfactant solution and homogenizing to break apart said first population of microcapsules or nanocapsules to form a second population of polymer microcapsules, nanocapsules, or mixtures thereof that are smaller in size then said first population;

(g) hardening said second population of polymer microcapsules, nanocapsules, or mixtures thereof by contacting with at least one hardening solvent comprising a drug which is dissolved or dispersed in said at least one hardening solvent to form a first population of drug-loaded polymer microcapsules, nanocapsules, or mixtures thereof in which at least 95% of the non polar solvent is removed;

(h) optionally removing traces of said at least one hardening solvent and thereby further hardening said first population of drug-loaded polymer microcapsules, nanocapsules, or mixtures thereof; and (i) removing said water soluble sublimable substance and said non water soluble sublimable substance if present from said drug-loaded population of polymer microcapsules, nanocapsules, or mixtures thereof to form echogenic drug-loaded polymer microcapsules, nanocapsules, or mixtures thereof which comprise at least 10% more of said drug as compared to (1) echogenic drug-loaded polymer microcapsules, nanocapsules, or mixtures thereof prepared by adding said drug prior to said emulsifying or (2) echogenic drug-loaded polymer microcapsules, nanocapsules, or mixtures thereof prepared by adding said drug to lyophilized polymer microcapsules, nanocapsules, or mixtures thereof.

In preferred embodiments, step (f) further includes adding an extraction solvent and stirring to begin removal of the non-polar solvent. The exemplary extraction solvent includes a solution of alcohol (e.g., iso-propanol) in water. As described in Examples below, 2% isopropananol in water is used as an extraction solvent. As used herein, the term "removal of the non-polar solvent" can include evaporation of the non-polar solvent as described in the Examples.

Further, additional amounts of the drug of choice can be added to any of the phases in preparation of mixtures or emulsions.

Pre-Hardening Stage Adsorption Method

In this method, the inventors have discovered that before lyophilization and just before the hardening stage of the capsules, they can be contacted with an aqueous solution of drug or solution of drug in a non solvent for the polymer but a solvent for the drug. An exemplary method demonstrating the pre-hardening stage adsorption is described in Examples 8 and 10.

Thus, in one aspect, the pre-hardening stage adsorption method for producing echogenic drug-loaded polymer microcapsules, nanocapsules, or mixtures thereof, comprises the following steps:

(a) forming a first mixture comprising a solution of at least one polymer in at least one volatile non-polar solvent and optionally at least one non-water soluble sublimable substance;

(b) forming a second mixture comprising a solution of at least one water soluble sublimable substance in at least one polar solvent;

(c) adding said first mixture to said second mixture to form a third mixture;

(d) emulsifying the third mixture to produce a first population of polymer microcapsules, nanocapsules, or mixtures thereof comprising said at least one polymer, said at least one water-soluble sublimable substance, and optionally, said at least one non-water sublimable soluble substance;

(e) mixing said first population of polymer microcapsules, nanocapsules, or mixtures thereof with a surfactant solution and homogenizing to break apart said first population of polymer microcapsules, nanocapsules, or mixtures thereof to form a second population of polymer microcapsules, nanocapsules, or mixtures thereof that are smaller in size then said first population;

(f) mixing said first population of polymer microcapsules, nanocapsules, or mixtures thereof with a surfactant solution and homogenizing to break apart said first population of polymer microcapsules, nanocapsules, or mixtures thereof to form a second population of polymer microcapsules, nanocapsules, or mixtures thereof that are smaller in size then said first population;

(g) contacting said second population of polymer microcapsules, nanocapsules, or mixtures thereof with a solution of a drug in a non-solvent for said polymer and thereby adsorbing at least a portion of said drug at least onto the surface of said second population of polymer microcapsules, nanocapsules, or mixtures thereof;

(h) removing said non-solvent having less of said drug due to said adsorbing at least a portion of said drug;

(i) hardening said second population of polymer microcapsules, nanocapsules, or mixtures thereof having adsorbed at least a portion of said drug by contacting with at least one hardening solvent to form a population of drug-loaded polymer microcapsules, nanocapsules, or mixtures thereof in which at least 95% of the non polar solvent is removed;

(j) optionally removing traces of said hardening solvent and thereby further hardening said population of drug-loaded polymer microcapsules, nanocapsules, or mixtures thereof; and (k) removing said water soluble sublimable substance and said non water soluble sublimable substance if present from said drug-loaded population of polymer microcapsules, nanocapsules, or mixtures thereof to form echogenic drug-loaded polymeric microcapsules or nanocapsules which comprise at least 10% more of said drug as compared to (1) echogenic drug-loaded polymer microcapsules, nanocapsules, or mixtures thereof prepared by adding said drug prior to said emulsifying or (2) echogenic drug-loaded polymer microcapsules, nanocapsules, or mixtures thereof prepared by adding said drug to lyophilized polymer microcapsules, nanocapsules, or mixtures thereof.

Further, additional amounts of the drug of choice can be added to any of the phases in preparation of mixtures or emulsions.

Figure 5:
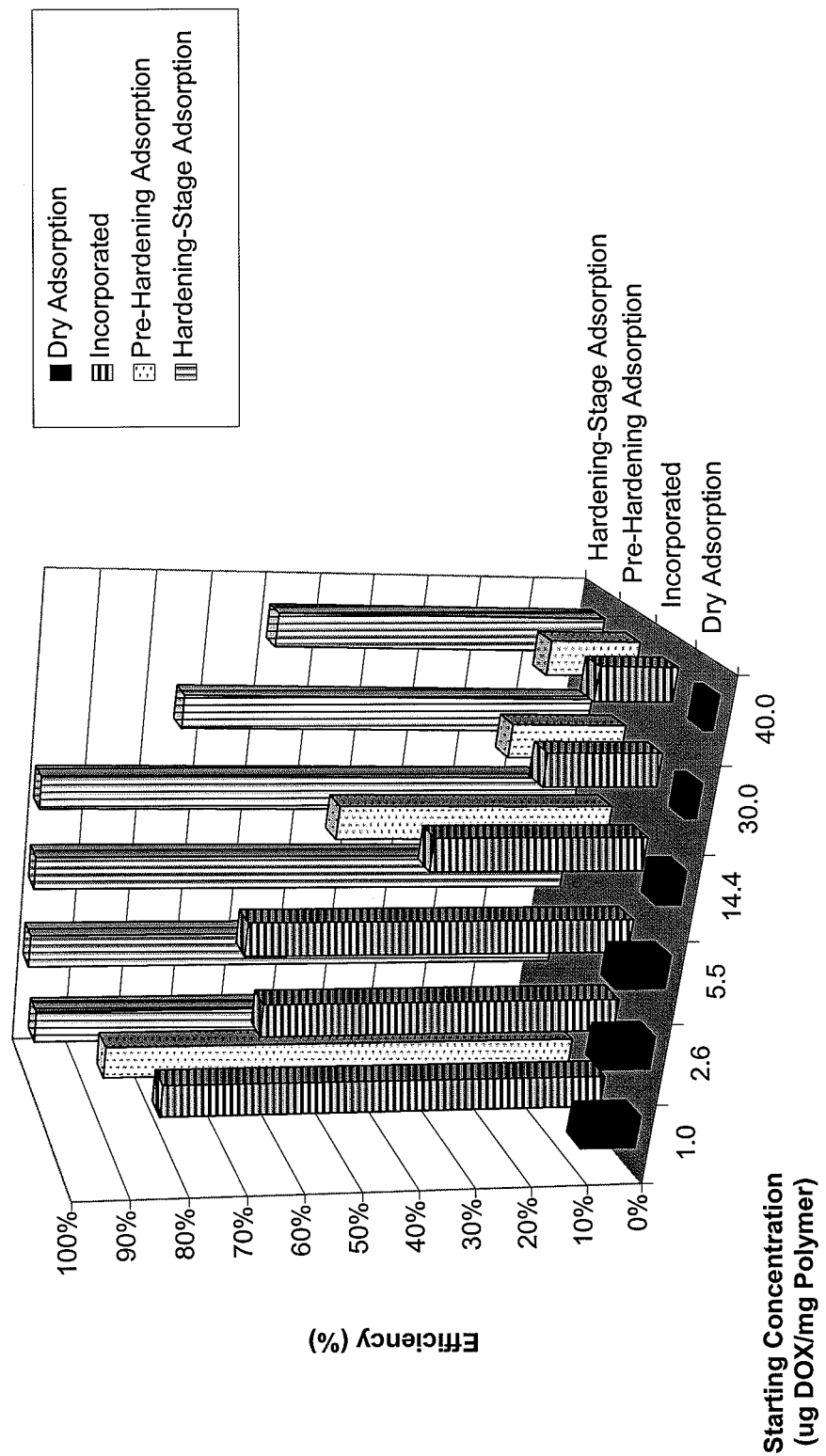
FIG. 5 is a bar graph demonstrating loading efficiency as a function of loading method and starting drug concentration for echogenic drug loaded capsules. Echogenic drug loaded capsules were made with camphor and ammonium carbonate as sublimable substances, PLA as a polymer, and Doxorubicin as drug.
Figure 6:
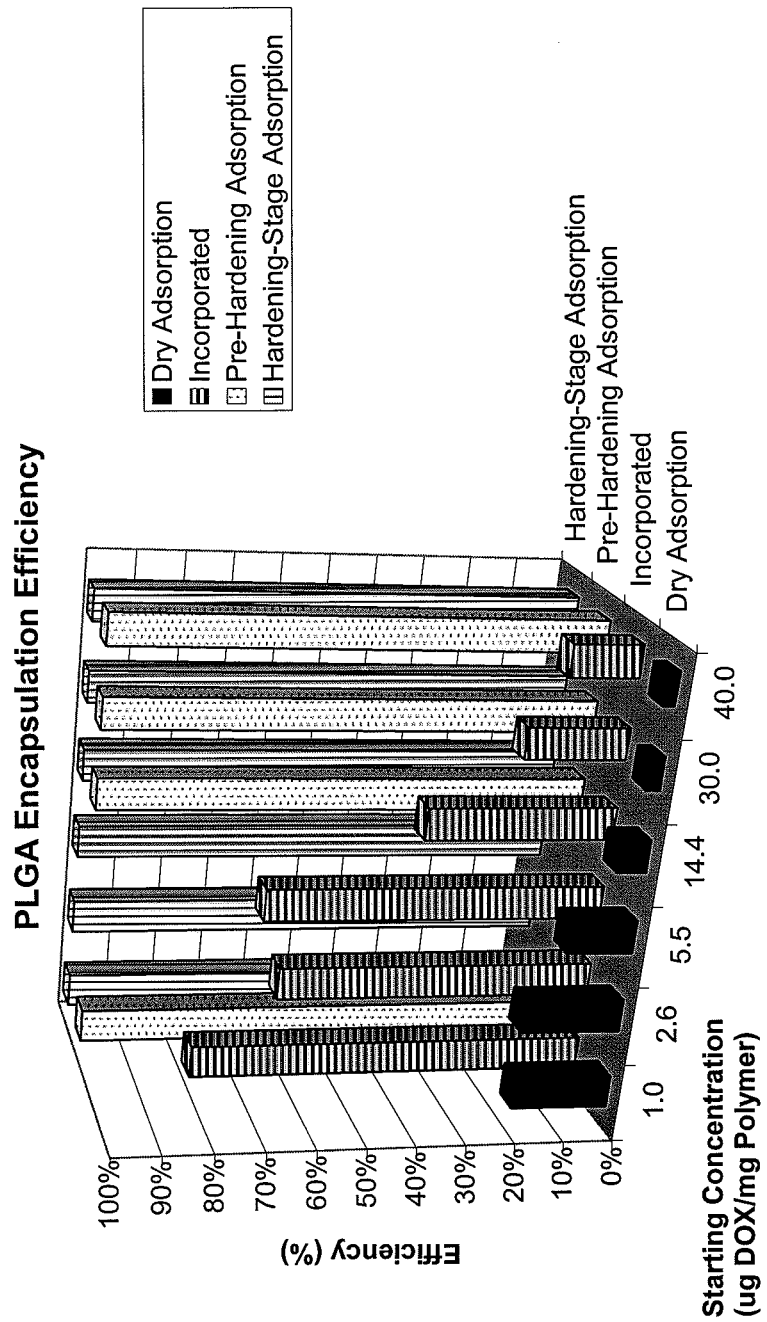
FIG. 6 is a bar graph demonstrating loading efficiency as a function of loading method and starting drug concentration for echogenic drug loaded capsules. Echogenic drug loaded capsules were made with camphor and ammonium carbonate as sublimable substances, PLGA as a polymer, and Doxorubicin as drug.

As compared to echogenic microcapsules or nanocapsules loaded with drugs using the known methods, the echogenic microcapsules or nanocapsules loaded with drugs using the methods of the invention contain at least 10 to 90% more of the drug. The hardening stage loading method is 90% more efficient than the dry adsorption method in the case of doxorubicin. FIGS. 5 and 6 demonstrate a comparison of efficiency of drug loading methods. As compared to echogenic microcapsules or nanocapsules loaded with drugs using the known methods, the echogenic microcapsules or nanocapsules loaded with drugs using the methods of the invention are at least 10 to 90% more efficient in adsorption of the drug, depending on loading conditions and previous method to which they are compared.

In one embodiment of the present invention, echogenic polymer microcapsules and/or nanocapsules are produced as follows. A non-water soluble substance capable of dissolving in one or more volatile non-polar solvents and capable of subliming, is first dissolved in one or more volatile non-polar solvents to form a first mixture. Any non-water soluble substance which dissolves in a non-polar solvent and sublimes from a solid state can be used to produce this first mixture. Examples include but are not limited to, camphor, camphene, naphthalene, cocoa butter and theobroma oil. Examples of non-polar solvents which can be used include, but are not limited to, methylene chloride, acetone, acetonitrile, tetrahydrofuran, chloroform, pentane, pentene, and methyl ethyl ketone. In a preferred embodiment, the non-water soluble substance is camphor and the solvent is methylene chloride. A preferred ratio of camphor to methylene chloride is 0.05 grams:10 ml. Additional non-polar solvents from the above-listed examples can also be added to the mixture to control the size of the capsules in the nano size range (nanocapsules). Addition of a second, preferably different solvent reduces the size of the capsules because of its different properties. For example, the rate at which the solvent leaves the capsules during the hardening phase affects the size of the capsules. Specifically, the faster the solvent leaves, the smaller are the capsules formed. Acetone leaves the capsules faster than methylene chloride. Accordingly, addition of acetone as a second solvent results in nanosized capsules in comparison to the microsized capsules formed when using only methylene chloride. To prepare drug loaded nanocapsules, the resulting (W/O) emulsion formed from the acetone containing mixture is then poured into 50 ml of 4° C., 5% polyvinyl alcohol solution and homogenized for 5 min at 9000 rpm. 100 ml of 2% isopropanol solution is then added to the double emulsion and stirred for one hour to evaporate the organic solvents. The microcapsules are then collected using centrifugation and washed three times with hexane. For hardening-stage incorporation, free drug (e.g., doxorubicin) is added in weights ranging from 0.5 g to 20 g to part (from about 2 ml) or all of the first hexane wash. Drug is stirred gently by swirling at room temperature for 5 minutes. Remaining hexane is then allowed to evaporate off the samples and hexane washing continued. The capsules are then flash frozen and lyophilized for 48 hours. Samples are stored at −20° C. in a desiccator until needed.

Alternatively, the (W/O) emulsion resulting from the acetone containing mixture is poured into 50 ml of 4° C., 5% polyvinyl alcohol solution and homogenized for 5 min at 9000 rpm. One hundred ml of 2% isopropanol solution is then added to the double emulsion and stirred for one hour to evaporate the organic solvents. The microcapsules are then collected using centrifugation. For the pre-hardening method of adding drug, drug is incorporated after centrifugation but before the hexane washing, by gently swirling the capsules with 2 ml of an aqueous solution containing drug (doxorubicin) in the range of 0.25-2.00 mg/ml for 5 minutes at room temperature. The microcapsules were then collected using centrifugation and washed three times with hexane. The capsules are then flash frozen and lyophilized for 48 hours. Samples are stored at −20° C. in a desiccator until needed.

For purposes of the present invention, by "nanocapsule" it is meant a capsule sufficiently small in size to access the microvasculature of the human body. Nanocapsules of the present invention range in size from about 10 nm to about 500 nm, while microcapsules of the present invention range in size from about 500 nm to about 1000 microns. Nanocapsules of this size provide an advantage in that they can access areas difficult if not impossible to reach with microcapsules. For example, nanocapsules can pass through leaky tumor vasculature. In addition, nanocapsules have different resonance frequencies thus providing advantages in both imaging and delivery of bioactive agents. Nanocapsules of the present invention have been found to be echogenic above 5 MHz. Furthermore, nanocapsules are cleared from the body at a slower rate than microcapsules, and they also tend to accumulate in a tumor site, a phenomenon known as the EPR effect, enhanced permeation and retention effect.

The term "drug" as used herein is not limited to a specific pharmacological agent or a bioactive agent. Non-limiting examples include antineoplastic agents, such as platinum compounds (e.g., spiroplatin, cisplatin, and carboplatin), methotrexate, fluorouracil, adriamycin, taxol, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon alpha-2a, interferon alpha-2b, teniposide (VM-26), vinblastine sulfate (VLB), vincristine sulfate, bleomycin, bleomycin sulfate, methotrexate, adriamycin, and arabinosyl, hydroxyurea, procarbazine, and dacarbazine; mitotic inhibitors such as etoposide and the vinca alkaloids, radiopharmaceuticals such as radioactive iodine and phosphorus products; hormones such as progestins, estrogens and antiestrogens; anti-helmintics, anti-malarials, and antituberculosis drugs; biologicals such as immune serums, antitoxins and antivenins; rabies prophylaxis products; bacterial vaccines; viral vaccines; aminoglycosides; respiratory products such as xanthine derivatives theophylline and aminophylline; thyroid agents such as iodine products and anti-thyroid agents; cardiovascular products including chelating agents and mercurial diuretics and cardiac glycosides; glucagon; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine; anti-fungal agents such as ketoconazole, nystatin, griseofulvin, flucytosine (5-FC), miconazole, amphotericin B, ricin, cyclosporins, and .beta.-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone terbutate, prednisone, triamcinolone, triamcinolone acetonide, triamcinolone diacetate, triamcinolone hexacetonide and fludrocortisone acetate, oxytocin, vassopressin, and their derivatives; vitamins such as cyanocobalamin neinoic acid, retinoids and derivatives such as retinol palmitate, and alpha-tocopherol; peptides, such as manganese super oxide dimutase; enzymes such as alkaline phosphatase; anti-allergic agents such as amelexanox; anti-coagulation agents such as phenprocoumon and heparin; circulatory drugs such as propranolol; metabolic potentiators such as glutathione; antituberculars such as paraminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), ribavirin and vidarabine monohydrate (adenine arabinoside, ara-A); antianginals such as diltiazem, nifedipine, verapamil, erythrityl tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin, including penicillin G, penicillin V, ticarcillin rifampin and tetracycline; antiinflammatories such as difunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as airacurium besylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium. Also magnetic resonance imaging agents such as superparamagnetic iron oxide gadopentetate dimeglumine, and mangafodipir trisodium and radioactive particles or ions such as strontium, iodide rhenium and yttrium can be added in the broad category of "drugs."

After the non-water soluble substance is fully dissolved in the non-polar solvent, a polymer material is added to the first mixture. Examples of polymers that can be used in this method include, but are not limited to, polylactide, a polyglycolide, a polycaprolactone, a copolymer of polylactide and polyglycolide, a copolymer of lactide and lactone, a polysaccharide, a polyanhydride, a polystyrene, a polyalkylcyanoacrylate, a polyamide, a polyphosphazene, a poly(methylmethacrylate), a polyurethane, a copolymer of methacrylic acid and acrylic acid, a copolymer of hydroxyethylmethacrylate and methylmethacrylate, a polyaminoacid, and a polypeptide. Preferred polymers are those which are biocompatible and/or biodegradable. In a preferred embodiment the polymer is polylactic co-glycolic acid (PLGA). In this embodiment it is preferred that 0.5 grams of the polymer be added to the 10 ml solution of the first mixture. In another preferred embodiment the polymer is polylactic acid (PLA).

The polymer is then stirred into the first mixture until it is completely dissolved, thus forming the second mixture.

A polar solvent, preferably water is added to the second mixture which is then emulsified. For emulsification with water, an aliquot of distilled water, preferably 1 ml, is added to a second mixture comprising 10 ml of methylene chloride, camphor and PLGA, and a probe sonicator is used for 30 seconds. This emulsion of a second mixture of methylene chloride, camphor and PLGA produces a population of microcapsules that range in size from 0.1 to 1 mm. In the context of the present invention this population of microcapsules is referred to as the first population of microcapsules.

The first population of microcapsules is then poured into a surfactant and homogenized for several minutes. Examples of surfactant which can be used in the present invention include, but are not limited to, poly(vinyl) alcohol (PVA), Tween and non-ionic surfactants. In a preferred embodiment, microcapsules of camphor and PLGA are added to 50 ml of a 5% PVA solution and homogenized for 5 minutes at 9,500 rpm. The addition of the surfactant allows for the break-up of the microcapsules into smaller beads to produce a second population of microcapsules and/or nanocapsules. This procedure enhances the size reduction of the microcapsules, an important step in the production process. In a preferred embodiment, the second population of microcapsules is poured into a solvent extraction agent such as, for example, 100 ml of a 2% isopropanol solution to initiate solvent extraction and stirred for one hour. This begins to remove residual methylene chloride to harden the microcapsules. Examples of solvent extraction agents that can be used at this step include, but are not limited to, isopropanol, ethanol, methanol, ethyl ether, petroleum ether, heptane, and hexane.

Following this initial solvent removal step, the microcapsules are collected by centrifugation, washed with excess distilled water, centrifuged again, and washed multiple times with a solvent such as hexane which removes the non-water soluble substance without dissolving the polymer. Hexane also acts as a hardening agent removing the residual methylene chloride further drying the capsules. After each wash, the wash solvent is removed by pipetting. A final washing with distilled water is then performed. The washed population of polymer microcapsules and/or nanocapsules are then centrifuged, frozen at −85° C., and then lyophilized to dry the capsules and remove any additional residual non-water soluble substance. This results in a free flowing powder of microcapsules and/or nanocapsules that is stable upon storage and can be resuspended routinely in a pharmaceutically acceptable vehicle such as saline just prior to use.

Drug loading can take place at various stages before and during the hardening steps. For pre-hardening, drug is incorporated after the isopropylalcohol step and centrifugation but before the hexane washing, by gently swirling the capsules with a polar solution containing drug. The microcapsules were then collected using centrifugation and washed three times with hexane. The capsules are then flash frozen and lyophilized for 48 hours. Samples are stored at −20° C. in a desiccator until needed.

For drug loading at the hardening stage, free drug is added to part or all of one of the hexane washes. Drug is stirred gently by swirling. Remaining hexane is then allowed to evaporate off the samples and hexane washing continued. The capsules are then flash frozen and lyophilized for 48 hours. Samples are stored at −20° C. in a desiccator until needed.

Particle size analysis of the final population of echogenic polymer microcapsules produced from camphor, methylene chloride and PLGA showed the population to be uniform in size with a range of 0.4 to 1.6 microns.

Acoustic dose-response experiments were performed using these echogenic drug-loaded polymer microcapsules. Four single element, broadband, 12.7 mm element diameter, 50.8 mm spherically focused transducers (Panametrics, Waltham, Mass.) with center frequencies of 2.25 MHZ, 5 MHZ, 7.5 MHZ and 10 MHZ, respectively, were chosen to represent the conventional medical ultrasound range. The 6 dB band widths of the transducers were 89%, 92%, 71% and 65% respectively. A known quantity (0.01 g to 1.0 g) of the echogenic polymer microcapsules was weighed into 50 ml of phosphate-buffered saline in a sample container and a dose-response was recorded. Doses on the dose-response curve were repeated six times. Fresh buffer was used at each dose and a 10 second delay post-administration of the agent in the container ensured proper mixing prior to collecting any signal. The signal was 2.0 ms time-gated, after the ringing from the wall signal had subsided. The root mean square (rms) of the gated signal was calculated, and the average for 50 A-lines with no agent (PBS only) was taken as base $S_0(t)$. Similarly, the average for 50 A-lines with contrast agent $S_{CA}(t)$ was calculated, and presented relative to $S_0(t)$ as enhancement ($\Sigma_E$) expressed in dB.

$$\Sigma_E = 20\log_{10}\left[\frac{\text{rms}\{s_{CA}(t)\}}{\text{rms}\{s_0(t)\}}\right]$$

The microcapsules of the present invention produced a dose-response relationship.

In another embodiment of the present invention, echogenic polymer microcapsules and/or nanocapsules can be produced in similar fashion to the above-described microcapsules with the following modifications. In the emulsification step, an agent which is dissolved in an aqueous solution and which sublimes is added. Examples of such agents which are water soluble and which sublime include, but are not limited to ammonium carbonate and other ammonium salts, theobromine and theobromine acetate. In a preferred embodiment, 1.0 ml of a 4% ammonium carbonate aqueous solution is added to the second mixture prior to probe sonication.

In another embodiment of the present invention, echogenic polymer microcapsules and/or nanocapsules can be produced in similar fashion to the above-described microcapsules with the following modifications. The non-water soluble substance which sublimes is omitted from the first step and polymer alone is dissolved in a non polar solvent, and in the emulsification step, an agent which is dissolved in an aqueous solution and which sublimes is added. Examples of such agents which are water soluble and which sublime include, but are not limited to ammonium carbonate, ammonium carbamate and other ammonium salts, theobromine and theobromine acetate. In a preferred embodiment, 1.0 ml of a 4% ammonium carbonate aqueous solution is added to the second mixture prior to probe sonication.

Size analysis using a Malvern nano ZS particle sizer showed mean diameters in the range of 0.8 to 1.6 microns. Size distribution analysis of microcapsules via Horiba size analysis revealed a mean diameter of 1.210 microns.

Figure 2:
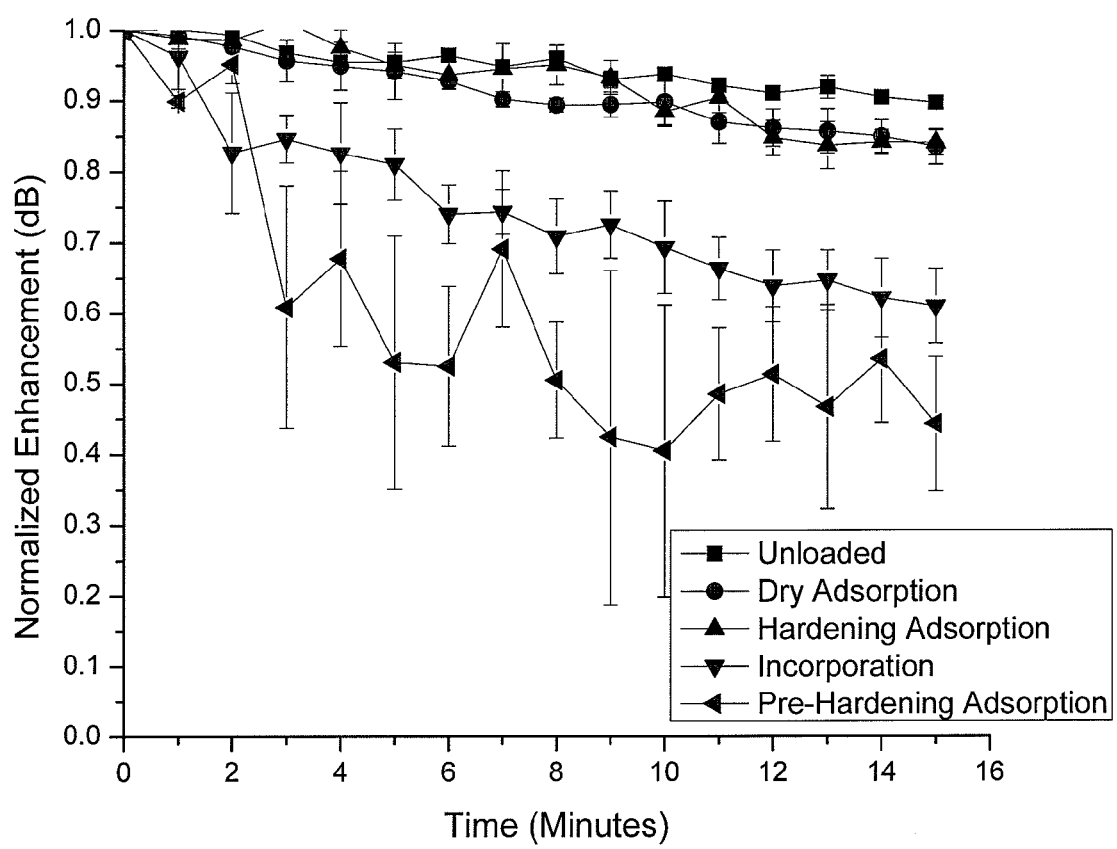
FIG. 2 demonstrates time response curves of contrast agents loaded with a drug by different methods. Echogenic drug loaded capsules were made with camphor and ammonium carbonate as sublimable substances, PLA as a polymer, and Doxorubicin as drug.

The polymer microcapsules prepared in accordance with this method using camphor and ammonium carbonate as sublimable substance and PLA showed that loading method affects echogenicity, drug loading reduces echogenicity compared to non loaded in all cases, maximum echogenicity (by loading method) is as follows: Pre-hardening stage adsorption (12.64 dB) less then Dry adsorption (14.4 dB) much less than Incorporation (17.28 dB) less than Hardening-stage adsorption (17.82 dB) less than no loading (19.65 dB) and dose at which maximum dB achieved follow the trend Hardening-stage adsorption (0.0075 mg/ml) equal to no loading (0.0075 mg/ml) less than Pre-hardening stage adsorption (0.0105 mg/ml) equal to Incorporation (0.0105) less than Dry adsorption (0.012 mg/ml). Numbers in brackets are values taken from FIG. 1. Although the pre-hardening stage adsorption method was not as efficient at preserving echogenicity as previous methods, echogenicity values were still acceptable. The hardening stage adsorption method of the invention provided capsules which were as good as capsules obtained in best previous method (incorporation). Both of which are comparable to a no-drug loaded agent. These results are in accordance with FIG. 1. Adding drug destabilized the agent when it is insonated at 5 MHz. The degree of destabilization is dependent on loading method. The half life t½ (time for the echogenicity to decay to half its initial value) of the agents is dependent on the method of drug loading. The t½ values compared to previous methods follow: Unloaded greater than Dry adsorption almost equal to Hardening stage adsorption greater than incorporation much greater than pre-hardening stage adsorption which equals 5 minutes. At 5 minutes unloaded and Dry adsorption and Hardening stage adsorption all have lost about 5%, Incorporation have lost 20% and pre-hardening adsorption have lost 50% of their original echogenicity. The hardening stage adsorption method is as good as previous methods. These results are in accordance with FIG. 2.

Figure 3:
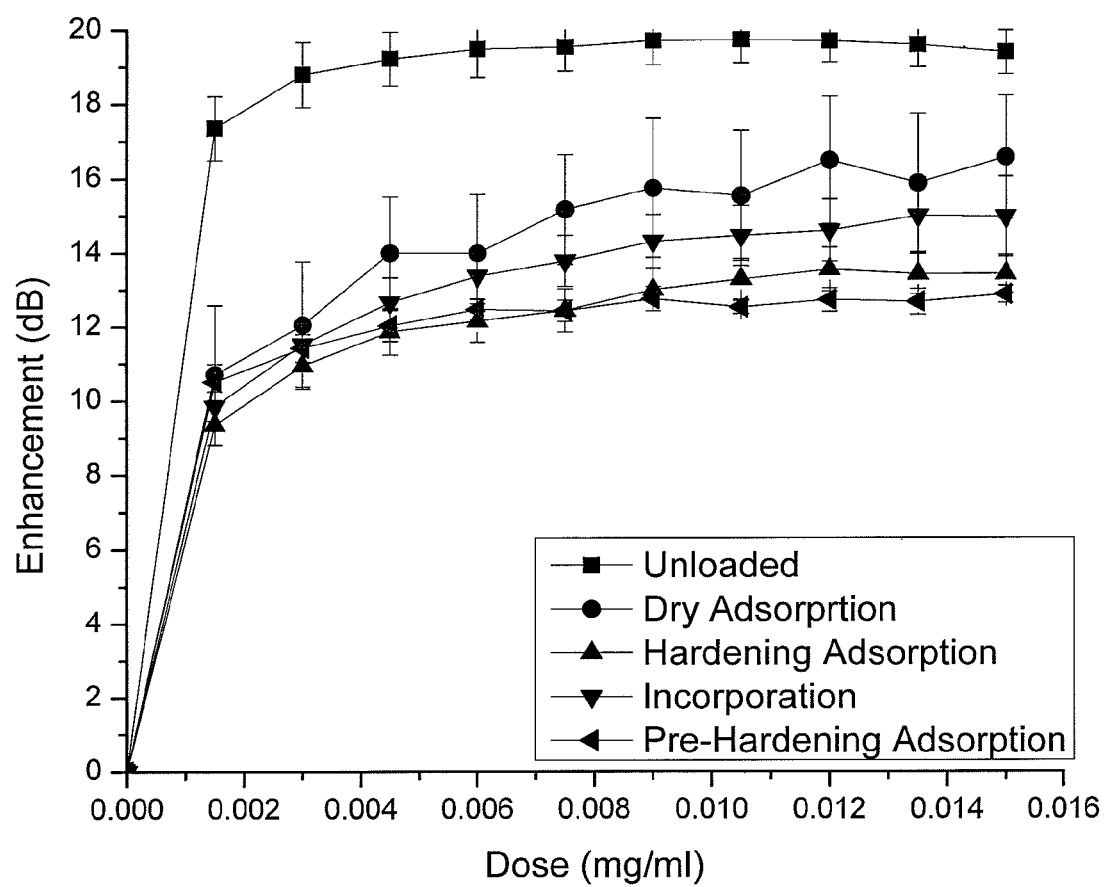
FIG. 3 demonstrates dose response curves of contrast agents loaded with a drug by different methods. Echogenic drug loaded capsules were made with camphor and ammonium carbonate as sublimable substances, PLGA as a polymer, and Doxorubicin as drug.

The polymer microcapsules prepared in accordance with this method using camphor and ammonium carbonate as sublimable substance and PLGA as polymer (in accordance with FIG. 3) showed that loading method affects echogenicity, drug loading reduces echogenicity compared to non loaded in all cases, maximum echogenicity (by loading method) is: Pre-hardening (12.6 dB) less than Hardening-stage adsorption (13.29 dB) less than Incorporation (14.75 dB)<Dry adsorption (16.25 dB)) much less than no loading (19.95 dB). Dose at which maximum dB achieved are: no loading (0.006 mg/ml) less than Dry adsorption (0.009 mg/ml) less than Pre-hardening (0.012) mg/ml) equal to Incorporation (0.012) equal to Hardening-stage adsorption (0.0012 mg/ml). The pre-hardening adsorption is not as good at preserving echogenicity as previous methods but still acceptable but hardening stage addition as good as best of the previous methods (incorporation) which is almost as good as the naïve, non drug loaded agent.

Adding drug destabilized the agent when it is insonated at 5 MHz. The degree of destabilization is dependent on loading method. The half life t½ (time for the echogenicity to decay to half its initial value) of the agents is dependent on the method of drug loading. The t½ values compared to previous methods follow:

At 8 minutes unloaded capsules have lost 15% of their original echogenicity; capsules prepared by a dry adsorption and a hardening stage adsorption methods both have lost 24% of their original echogenicity; capsules prepared by an incorporation method have lost 42% and capsules prepared by a pre-hardening adsorption method have lost 50% of their original echogenicity.

Figure 4:
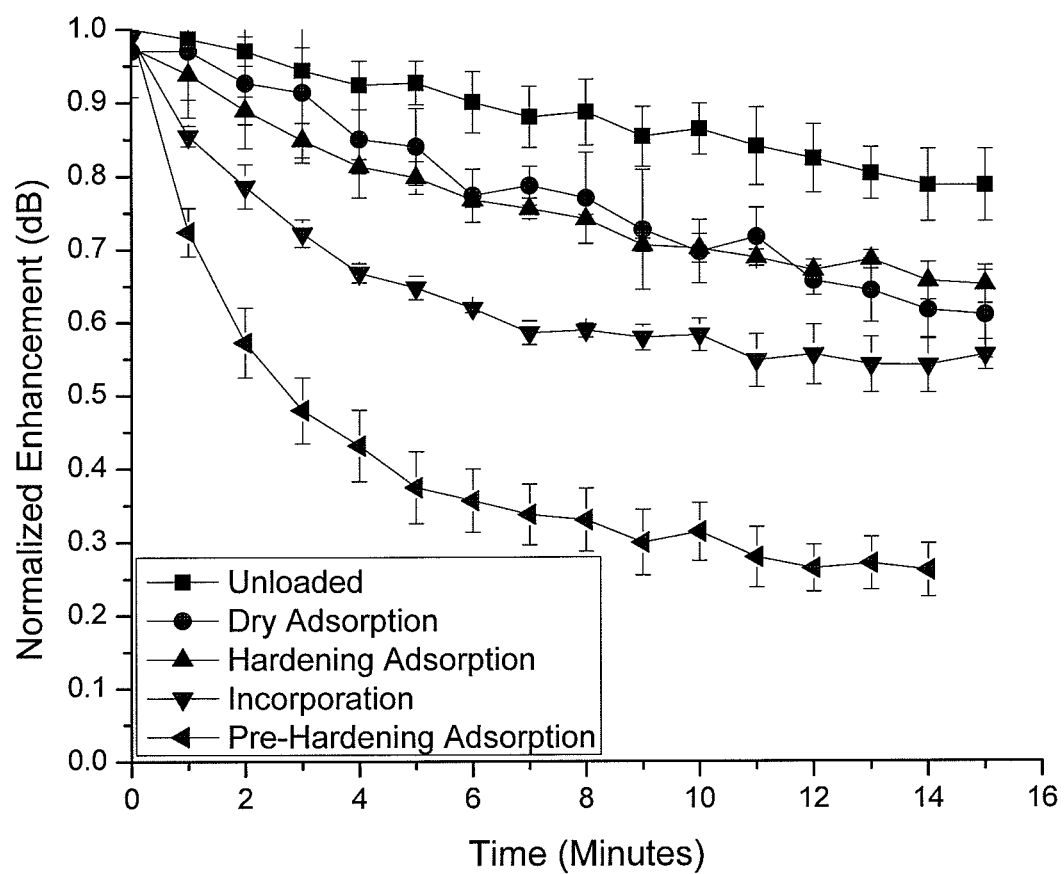
FIG. 4 shows time response curves of PLGA contrast agent loaded by different methods of drug loading. Capsules made with camphor and ammonium carbonate as sublimable substances.

Capsules loaded by the incorporation method had shown a relatively rapid initial loss which reached a plateau of 45% loss at 10 minutes. These results are in accordance with FIG. 4.

The hardening stage adsorption method produces capsules that are as stable as capsules produced by the dry adsorption method and slightly less stable than unloaded capsules.

The choice of polymer informs the end use of the agent. For example, in drug delivery situations, a less stable but highly drug loaded agent may be desired. Drug loading by the hardening stage method has only a small effect on the echogenicity for PLA but a more significant effect for PLGA capsules. All drug loading mechanisms have a significant effect for PLGA capsules that is similar in degree to the effect of drug loading by the hardening stage method on PLA capsules.

The effect of polymer choice is demonstrated by the fact that drug loaded capsules of PLA are more stable than those of PLGA. These results are in accordance with comparing FIGS. 1 and 2 with FIGS. 3 and 4, respectively. In vivo grey scale imaging was also performed in New Zealand White rabbits using microcapsules loaded with sudan black as the imaging agent and showed excellent enhancement of the image in comparison to imaging taken without the agent.

Thus, as demonstrated herein, echogenic polymer microcapsules and nanocapsules produced in accordance with these methods can be loaded with drug and used for drug delivery and imaging of any of the various tissues and epithelium and/or endothelium thereof routinely imaged with ultrasound techniques including, but not limited to, renal tissue, brain tissue, tumor vasculature, skin tissue, pancreatic tissue, breast tissue, heart tissue, prostate tissue, uterine tissue, adrenal gland tissue, retinal tissue, muscle tissue, areas of plaque and areas of ischemia.

In another aspect, the invention is echogenic drug-loaded polymer microcapsules, nanocapsules, or mixtures thereof produced by the method of the invention wherein the echogenic drug-loaded polymer microcapsules, nanocapsules, or mixtures thereof comprise at least 10% more of a drug as compared to (1) echogenic drug-loaded polymer microcapsules, nanocapsules, or mixtures thereof prepared by adding said drug prior to said emulsifying or (2) echogenic drug-loaded polymer microcapsules, nanocapsules, or mixtures thereof prepared by adding drug to lyophilized polymer microcapsules, nanocapsules, or mixtures thereof.

For use as a contrast agent, it is preferred that the echogenic drug-loaded microcapsules and/or nanocapsules of the present invention be hollow or porous so that they can be filled with gas. Such gas-filled polymer microcapsules are produced by introducing echogenic hollow or porous polymer microcapsules into contact with a gas and equilibrating the microcapsules with the gas for a period of time sufficient to allow diffusion of the gas into the polymer microcapsules, resulting in a gas-filled polymer microcapsule. This procedure of exposing hollow or porous polymer microcapsules to the gas may be carried out at ambient pressure (atmospheric), at sub-atmospheric pressure, or at an elevated pressure. The period of time required to effect filling of the hollow microcapsules with the gas is relatively short, typically requiring only a few minutes, the actual time depending on the manner and pressure at which the hollow microcapsules are equilibrated with the gas. The term "gas" as used in this specification includes substances which are in gaseous form under normal storage conditions, e.g., at about 15 to 25° C., and/or at normal mammalian body temperature, e.g., 37° C. in humans. The resulting gas-filled polymer drug loaded microcapsules of this invention may be stored as a dry, free-flowing powder, preferably in the presence of the gas contained in the polymer nano or microcapsules.

The gas-filled microcapsules are useful as contrast agents in medical imaging, such as diagnostic ultrasound. Ultrasound contrast compositions typically comprise the hollow or porous polymer microcapsules, filled with a gas, and dispersed in an aqueous liquid which serves as a carrier for the contrast agent. Aqueous liquids that can be used include, but are not limited to, isotonic saline and phosphate-buffered saline. The contrast agent composition is then injected into the bloodstream and used for ultrasound visualization of specific blood vessels or body organs.

The polymer microcapsules and nanocapsules of the present invention can be used for delivery of bioactive agents. In this embodiment, a bioactive agent may be adsorbed to and/or attached to the surface of the microcapsule or nanocapsule at various stages of capsule preparation, either before hardening, during hardening or after the preparation of the microcapsules and nanocapsules. The resulting microcapsules and/or nanocapsules are then washed, frozen and lyophilize. The lyophilized microcapsules have the drug product to be delivered adsorbed to their surfaces. Bioactive agents can also be attached to the microcapsules and/or nanocapsules in accordance with well known methods for conjugation. For example, a conjugation method such as taught in Example 15 may be used substituting the bioactive agent for the RGD peptide. Alternatively, or in addition, a bioactive agent can be encapsulated in the microcapsule or nanocapsule. Water soluble bioactive agents can be encapsulated in the microcapsules or nanocapsules by including water during emulsification and dissolving the bioactive agent in this water. Non-water soluble bioactive agents can be encapsulated in the microcapsules or nanocapsules by dissolving the bioactive compound in the non-polar organic solvent in the first step of preparation of these capsules. Examples of bioactive agents which can be adsorbed, attached and/or encapsulated in the microcapsules and/or nanocapsules of the present invention include, but are not limited to, antineoplastic and anticancer agents such as azacitidine, cytarabine, fluorouracil, mercaptopurine, methotrexate, thioguanine, bleomycin peptide antibiotics, podophyllin alkaloids such as etoposide, VP-16, teniposide, and VM-26, plant alkaloids such as vincristine, vinblastin and paclitaxel, alkylating agents such as busulfan, cyclophosphamide, mechlorethamine, melphanlan, and thiotepa, antibiotics such as dactinomycin, daunorubicin, plicamycin and mitomycin, cisplatin and nitrosoureases such as BCNU, CCNU and methyl-CCNU, anti-VEGF molecules, gene therapy vectors and peptide inhibitors such as MMP-2 and MMP-9, which when localized to tumors prevent tumor growth.

Once prepared, microcapsules and/or nanocapsules comprising the bioactive agent can be suspended in a pharmaceutically acceptable vehicle for injection into animals, including humans. Once injected, the bioactive agent is released by either biodegradation over time of the polymer microcapsule structure, by initiation of release of the bioactive agent through exposure to ultrasound, or by a combination thereof.

Compositions of the present invention can be used to direct delivery of a bioactive agent to any of the various tissues and epithelium and/or endothelium thereof including, but not limited to, renal tissue, lung tissue, brain tissue, tumor vasculature, skin tissue, pancreatic tissue, breast tissue, heart tissue, prostate tissue, intestinal tissue, uterine tissue, adrenal gland tissue, retinal tissue, muscle tissue, areas of plaque, areas of inflammation, and areas of ischemia.

The microcapsules and/or nanocapsules of the present invention may further comprise a targeting agent attached to the capsule surface which upon systemic administration can target the contrast agent or the delivery agent to a selected tissue or tissues, or cell in the body. Targeting agents useful in the present invention may comprise peptides, antibodies, antibody fragments, or cell surface receptor-specific ligands that are selective for a tissue or cell. Examples include, but are in no way limited to, RGD which binds to alpha.v integrin on tumor blood vessels, NGR motifs which bind to aminopeptidase N on tumor blood vessels, signal transduction molecules which when attached to the cell trigger an intracellular cascade such as tumor necrosis factor apoptosis inducing ligand (TRAIL) and ScFvc, which binds to the EBD domain of fibronectin. Accordingly, targeting agents can be routinely selected so that a contrast agent or delivery agent of the present invention, or a combination thereof, is directed to a desired location in the body such as selected tissue or tissue cells or an organ, or so that the contrast agent or delivery agent of the present invention can distinguish between various tissues such as diseased tissue versus normal tissue or malignant tissue versus benign tissue or so that attachment causes a specific event to be initiated inside the cell. Targeted contrast and/or delivery agents can be administered alone or with populations of contrast agents and/or delivery agents of the present invention which do not further comprise a targeting agent.

The following observations were made:
(a) echogenicity of drug loaded PLA and PLGA microbubbles is affected by the loading method;
(b) echogenicity of drug loaded PLA and PLGA microbubbles is affected by polymer;
(c) stability during insonation is affected by the loading method;
(d) stability during insonation is affected by the polymer;
(e) quantity of drug loaded PLA and PLGA microbubbles is affected by the loading method;
(f) quantity of drug loaded PLA and PLGA microbubbles is affected by polymer;
(g) loading efficiency of drug onto loaded PLA and PLGA microbubbles is affected by polymer;
(h) loading efficiency of drug onto loaded PLA and PLGA microbubbles is affected by the loading method;
(i) drug release can be triggered using ultrasound beam; and
(j) qualitative in vivo experiments show the potential of using the CA as carriers for drugs in physiological environment.

The following non-limiting examples are provided to further illustrate the present invention.

EXAMPLES

Example 1

Materials

Poly(D,L,-lactic-co-glycolic acid) acid 50:50, (PLGA) was purchased from Lakeshore Biomedical, Poly (vinyl alcohol) (PVA), 88% mole hydrolyzed, with a M.sub.w of 25,000 was purchased from Polysciences, Inc. (1R)-(+)-Camphor, Ammonium Dihydrogen Phosphate, GRGDS (Gly-Arg-Gly-Asp-Ser) peptide complex, EDC (1-Ethyl-3,-3-Dimethylamino-Pr-opyl) carbodiimide, NHS (N-Hydroxysulfosuccinimide), Antibiotics (penicillin and streptomycin), and L-glutamine were from Sigma. Dulbecco's Modified Eagle Medium (DMEM), Hank's Balanced Salt Solution, sodium pyruvate, non-essential amino acids for DMEM, vitamins for DMEM and Fetal Bovine Serum (FBS) were purchased from Fisher. Ammonium Carbonate and carbamate were purchased from J. T. Baker. All other chemicals were reagent grade from Fisher. Human breast adenocarcinoma cells (MDA-MB-231) were purchased from ATCC, Manassas, Va. Doxorubicin was purchased from Sigma.

Example 2

Particle Sizing and Zeta Potential

Particle sizing and zeta potential measurements were done on a Nano ZS Particle Sizer (Malvern) in order to quantify physical properties of the agent. One mg of dry sample was added to 1 ml of DI water. The sample was vortexed for 30 seconds and pippetted into a cuvette for measuring. The sample was allowed to sit for 2 minutes before measurement to avoid the measurement of air bubbles that may have formed during vortexing and pippeting. Three runs of 25 readings were run on the particle sizer to measure particle size by intensity. Size quality reports we collected to ensure statistically significant results. Zeta potential and size distribution were then calculated automatically by the Nano ZS software and exported.

Example 3

SEM Imaging

Prepared agents were imaged using an environmental scanning electron microscope (FEI XL30). Dry agent was sputter coated with platinum for 80 seconds prior to imaging. All images were taken at a magnification of 3000× at an accelerating voltage of 10.0 kV All imaging is done at the Drexel University Materials Characterization Facility.

Example 4

Acoustic Testing: Dose Response Curve

Acoustic enhancement and stability under ultrasonic conditions were both measured in vitro to determine microbubble performance. A pulse-echo setup was used. It consisted of a 5 MHz transducer (Panametrics, interchangeable with other transducers from 2.5 MHz to 25 MHz) with a 12.7 mm diameter, focal length of 50.8 mm, −6 dB bandwidth of 91% and a pulse length of 1.2 mm was placed in a 25° C. water bath with 18.6 MΩ-cm deionized water. The transducer was focused through the acoustically transparent window at a depth of roughly 14 cm from the surface to correspond to a hydrostatic pressure these agents will experience in vivo. A pulser/receiver (5072 PR Panametrics Inc.) was used to generate a pulse repetition frequency of 100 Hz. Received responses were then amplified 40 dB and read in an oscilloscope (Lecroy 9350 A). Data was then acquired using LabView 7 Express (National Instruments) and stored on a Dell CPU for later calculation.

To measure backscattering enhancement as a function of sample dosage, the sample holder was filled with 50 mL of PBS at 37° C. 3 mg of dry agent was suspended in 800 μl of PBS. Samples were then pipetted into the sample holder in incremental dosages and allowed to mix for 10 seconds. Enhancement was then measured for each dosage ranging from 0-16 μg/ml. All values were based on an average of three readings from three individual samples.

Example 5

Acoustic Testing: Time Response (Stability) Curve

Contrast agent stability under ultrasonic conditions was measured in order to determine whether the agents would last for the duration of an ultrasound imaging session. A dose chosen on the rise of the dose response curve (usually equivalent to roughly 4 µg/ml of sample) was added to 50 ml of 37° C. PBS and continually stirred and insonated with the setup described above. Enhancement was measured every minute for 15 minutes and the results normalized with respect to initial enhancement. All values were based on an average of three readings from three individual samples.

Example 6

Statistical Analysis

A One-way ANOVA was used to determine statistical significance and was performed using Prism 3.0 (GraphPad). Statistical significance was determined using α=0.05. A Newman-Keuls test was performed as a post test to determine significant variance between groups.

Example 7

Preparation of Drug Loaded Contrast Agent Using Hardening Stage Adsorption (Water-Soluble and Non-Water Soluble Porogens)

Microbubbles are prepared using a double emulsion (W/O)/W process. Usually 0.5 g of PLA and 0.05 g of camphor are dissolved in 10 ml of methylene chloride. One ml of 4% (w/v) ammonium carbonate is added and the mixture sonicated at 110 Watts for 30 seconds at 3 seconds on and 1 second off. The resulting (W/O) emulsion is then poured into 50 ml of 4° C., 5% polyvinyl alcohol solution and homogenized for 5 min at 9000 rpm. One hundred ml of 2% isopropanol solution is then added to the double emulsion and stirred for one hour to evaporate the organic solvents. The microcapsules are then collected using centrifugation and washed three times with hexane. For hardening-stage adsorption, free drug (e.g., doxorubicin) is added in weights ranging from 0.5 g to 20 g to part (from about 2 ml) or all of the first hexane wash. Drug is stirred gently by swirling at room temperature for 5 minutes. Remaining hexane is then allowed to evaporate off the samples and hexane washing continued. The capsules are then flash frozen and lyophilized for 48 hours to remove substances that sublime. Samples are stored at −20° C. in a desiccator until needed.

Example 8

Preparation of Drug Loaded Contrast Agent-Pre-Hardening-Stage Adsorption (Water-Soluble and Non-Water Soluble Porogens)

Microbubbles are prepared using a double emulsion (W/O)/W process. Usually 0.5 g of 50:50 PLGA and 0.05 g of camphor are dissolved in 10 ml of methylene chloride. One ml of 4% (w/v) ammonium carbonate is added and the mixture sonicated at 110 Watts for 30 seconds at 3 seconds on and 1 second off. The resulting (W/O) emulsion is then poured into 50 ml of 4° C., 5% polyvinyl alcohol solution and homogenized for 5 min at 9000 rpm. One hundred ml of 2% isopropanol solution is then added to the double emulsion and stirred for one hour to evaporate the organic solvents. The microcapsules are then collected using centrifugation.

For the pre-hardening method of drug loading, a drug is incorporated after centrifugation but before the hexane washing, by gently swirling the capsules with 2 ml of an aqueous solution containing drug (e.g., doxorubicin) in the range of 0.25-2.00 mg/ml for 5 minutes at room temperature. The microcapsules were then collected using centrifugation and washed three times with hexane. The capsules are then flash frozen and lyophilized for 48 hours to remove substances that sublime. Samples are stored at −20° C. in a desiccator until needed.

Example 9

Preparation of Drug Loaded Contrast Agent—a Hardening Stage Adsorption Method (Capsules are Made with Only Ammonium Carbamate as Porogen in Polar Solvent)

Microbubbles are prepared by a double emulsion (W/O)/W solvent evaporation process. Poly (D,L-lactic acid) (PLA) or Poly (D,L lactic-co-glycolic acid) (PLGA) (0.50 g) is dissolved in methylene chloride (10 ml), and ammonium carbamate (1 ml) (1M) solution is added. The polymer solution is probe sonicated at 110 W for 30 s. The resulting (W/O) emulsion is then poured into cold (4° C.), polyvinyl alcohol solution (5%) and homogenized for 5 min at 9000 rpm. The double emulsion is then poured into a 2% isopropanol solution and stirred at room temperature for 1 hour. The capsules are then collected by centrifugation and washed three times with hexane. For hardening-stage incorporation, free drug (e.g., doxorubicin) is added in weights ranging from 0.5 mg to 20 mg to part (from about 2 ml) one or all of the hexane washes. Drug is stirred gently by swirling at room temperature for 5 minutes. Remaining hexane is then allowed to evaporate off the samples and hexane washing continued. The capsules are then flash frozen and lyophilized for 48 hours to remove substances that sublime. Samples are stored at −20° C. in a desiccator until needed.

Example 10

Preparation of Drug Loaded Contrast Agent—a Pre-Hardening-Stage Adsorption Method (Capsules are Made with Only Ammonium Carbamate as Porogen in a Polar Solvent)

Microbubbles are prepared by a double emulsion (W/O)/W solvent evaporation process. Poly (D,L-lactic acid) (PLA) or Poly (D,L lactic-co-glycolic acid) (PLGA) (0.50 g) is dissolved in methylene chloride (10 ml), and ammonium carbamate (1 ml) (1M) solution is added. The polymer solution is probe sonicated at 110 W for 30 s. The resulting (W/O) emulsion is then poured into cold (4° C.), polyvinyl alcohol solution (5%) and homogenized for 5 min at 9000 rpm. The double emulsion is then poured into a 2% isopropanol solution and stirred at room temperature for 1 hour. The capsules are then collected by centrifugation. For the pre-hardening method of adding drug, drug is incorporated after centrifugation but before the hexane washing, by gently swirling the capsules with 2 ml of an aqueous solution containing drug (doxorubicin) in the range of 0.25-2.00 mg/ml for 5 minutes at room temperature. The microcapsules are then collected using centrifugation and washed three times with hexane to harden the capsules. The capsules are then flash frozen and lyophilized for 48 hours to remove substances that sublime. Samples are stored at −20° C. in a desiccator until needed.

Example 11

Preparation of Drug Loaded Contrast Agent Using a Hardening Stage Adsorption Method (a Prophetic Example)

Microbubbles will be prepared using a double emulsion (W/O)/W process. Usually 0.5 g of PLA and 0.05 g of camphor are to be dissolved in 10 ml of methylene chloride. One ml of distilled water is added and the mixture sonicated at 110 Watts for 30 seconds at 3 seconds on and 1 second off. The resulting (W/O) emulsion is then poured into 50 ml of 4° C., 5% polyvinyl alcohol solution and homogenized for 5 min at 9000 rpm. One hundred ml of 2% isopropanol solution is then added to the double emulsion and stirred for one hour to evaporate the organic solvents. The microcapsules are then collected using centrifugation and washed three times with hexane. For hardening-stage adsorption, free drug (e.g., doxorubicin) is added in weights ranging from 0.5 mg to 20 mg to part (from about 2 ml) or all of the first hexane wash. Drug is stirred gently by swirling at room temperature for 5 minutes. Remaining hexane is then allowed to evaporate off the samples and hexane washing continued. The capsules are then flash frozen and lyophilized for 48 hours. Samples are stored at −20° C. in a desiccator until needed.

Example 12

Drug Loaded Nanocapsules

Nanocapsules contrast agent can be prepared using a single emulsion method. Camphor (~0.004 g) and PLA (~00.075 g) are dissolved in acetone (5 ml) and sonicated at 110 W for 15 seconds. The solution is added to 100 ml of 1% poly(vinyl alcohol) (PVA and homogenized for 7 minutes at 12,000 rpm. After homogenization, the mixture is poured into 100 ml of deionized water, and stirred using a large stir bar on a magnetic stir plate overnight in the fume hood to evaporate the acetone. The nanocapsules are then collected using centrifugation and washed three times with hexane. For a hardening stage adsorption method, a solid drug (e.g., doxorubicin) is added in weights ranging from 0.5 mg to 20 mg to part (from about 2 ml) or all of the first hexane wash. Drug is stirred gently by swirling at room temperature for 5 minutes. Remaining hexane is then allowed to evaporate off the samples and hexane washing continued. The capsules are then flash frozen and lyophilized for 48 hours. Samples are stored at −20° C. in a desiccator until needed.

Example 13

Estimation of Drug Loading Efficiency

Encapsulation efficiency was measured to determine how much drug was encapsulated within the microbubble and how efficiently the amount of drug being loaded was encapsulated. Doxorubicin (DOX) is a hydrophilic substance having MW of 579.99 g/mol. It is used as anti cancer drug which interferes with DNA duplication after entering a cancerous cell. It is naturally fluorescent, excitation wavelength of 365 nm and an emission wavelength of 450 nm. which helps greatly in analysis. Three mg of sample of drug-loaded contrast agent was dissolved in 1 ml of deionized water and shaken at 37° C. for 7 days to dissolve the polymer and release all encapsulated drug. After incubation, samples were centrifuged for 5 min at 5000 rpm to separate lactide and glycolide monomers from the DOX solution. 200 µL samples were taken from the supernatant and the fluorescence read. A calibration curve in the same range of concentration was prepared in order to determine the amount of DOX in the samples.

Example 14

Drug Loading

Drug loading was calculated by dividing the weight of drug measured in sample by the weight of sample dissolved. Encapsulation efficiency was calculated as the ratio of drug encapsulation to the amount of drug loading attempted.

Example 15

Coating of Microcapsules with RGD Peptide

Dried drug loaded microcapsules (100 mg) can be combined with 5 mg 1-ethyl-3-(dimethylamino-propyl)-carbodiimide (EDC) (1:1 mole ratio of COOH groups), 1.4 mg of N-hydroxysuccinimide (NHS) (1:2 mole ratio to EDC), in 10 ml of buffer (0.1 M MES, 0.3M NaCl, pH 6.5) and stirred for 15 minutes. RGD peptide (150 µg) is then added and stirred for 24 hours. The microcapsules are washed with deionized water three times and lyophilized.

Example 16

Static Cell Attachment Study

To test the targeting ability of the ultrasound contrast agents in vitro, a cell attachment study is performed. MDA-MB-231 human breast cancer cells are grown on tissue culture plates in RPMI 1640 cell growth medium supplemented with 10% fetal bovine serum (FBS) and 1% penicillin-streptomycin. At passage 3 cells are plated in 48-well plates. Microbubbles ligated with the amino acid sequence Gly-Arg-Gly-Asp-Ser (GRGDS) are suspended in the above described supplemented cell growth medium (0.5 mg/ml). For use as a control, unligated microbubbles are also suspended in supplemented cell growth medium (0.5 mg/ml). 1 ml of the respective microbubble suspension is added to each well (n=3). As a second control, cells with integrin receptors pre-blocked is created by adding excess GRGDS peptide and incubating cells at 37° C. and 5% $CO_2$ for 1 hr prior to testing. To these receptor blocked cells, 1 ml of the RGD ligated microbubbles is added. Cells are incubated with the microbubble suspensions at 37° C. and 5% $CO_2$. At time points 0, 10, and 20 minutes, cells are washed 3× with sterile media and imaged with an Olympus IX microscope using spot software. Microbubble attachment/cell is determined through visual inspection. Statistical significance is determined using GraphPad Prism software (GraphPad Software, Inc., San Diego, Calif.).

Example 17

Ultrasound Triggering of Drug Release

Ultrasound triggered drug release was measured in the described acoustic setup in 20 mg of sample was suspended in 3 ml of DI water and added to sample holder containing 50 ml of PBS. For this example, echogenic microcapsules were made using the dry adsorption method as describe above, wherein DOX was loaded onto capsules after the lyophilization step.

Figure 7:
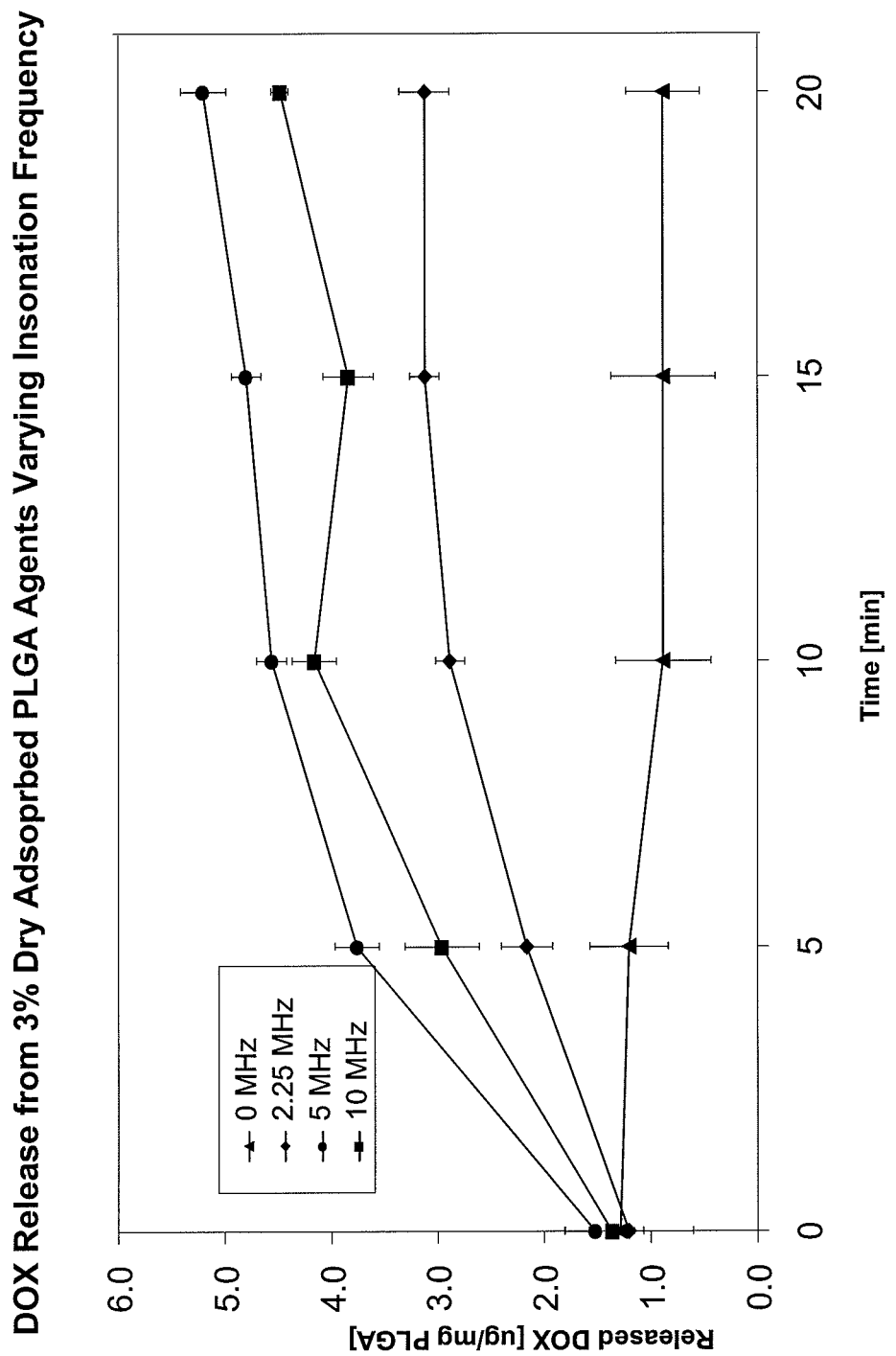
FIG. 7 is a graph demonstrating ultrasound triggered drug release with time as a function of insonation frequency. Echogenic drug loaded capsules were made with camphor and ammonium carbonate as sublimable substances, PLGA as a polymer, and Doxorubicin as drug.

One ml of the solution from the sample holder was then taken and pipetted into a micro centrifuge tube. The ultrasound was then turned on and allowed to run for twenty minutes. Ultrasound conditions can be changed by variables such as, but not limited to, transducer frequency, pressure, and pulse repetition frequency. One ml of sample was taken every five minutes for the duration of the ultrasound exposure. Immediately after each sample was taken, it was centrifuged for 5 minutes at 5000 rpm to separate free polymer from released drug. The supernatant was then sampled in 200 µL increments and the fluorescence read to calculate the amount of drug release in solution. Controls were performed repeating the experiment with no ultrasound exposure. All samples were measured in triplicates for statistical analysis (see FIG. 7). It was observed that the release of the drug (a) increases when the sample is being insonated, (b) time dependent, and (c) frequency dependent, e.g., for this particular sample in the order 2.25 MHz less than 10 MHz less than 5 MHz.

While the invention has been described in detail and with reference to specific examples thereof, it will be apparent to one skilled in the art that various changes and modifications can be made therein without departing from the spirit and scope thereof.

What is claimed:

1. A hardening stage adsorption method for producing echogenic doxorubicin-loaded polymer microcapsules, nanocapsules, or mixtures thereof, the method comprising:
    (a) forming a first mixture comprising a solution of poly (D,L-lactic acid) (PLA) in at least one volatile non-polar solvent and optionally at least one non-water soluble sublimable substance;
    (b) forming a second mixture comprising a solution of at least one water soluble sublimable substance in at least one polar solvent;
    (c) adding said first mixture to said second mixture to form a third mixture;
    (d) emulsifying the third mixture to produce a first population of polymer microcapsules, nanocapsules, or mixtures thereof comprising PLA, said at least one water-soluble sublimable substance, and optionally, said at least one non-water sublimable soluble substance;
    (e) mixing said first population of polymer microcapsules, nanocapsules, or mixtures thereof with a surfactant solution and homogenizing to break apart said first population of microcapsules or nanocapsules to form a second population of polymer microcapsules, nanocapsules, or mixtures thereof that are smaller in size than said first population;
    (f) hardening said second population of polymer microcapsules, nanocapsules, or mixtures thereof by contacting with at least one hardening solvent comprising doxorubicin dissolved or dispersed in said at least one hardening solvent to form a first population of doxorubicin-loaded polymer microcapsules, nanocapsules, or mixtures thereof in which at least 95% of the non-polar solvent is removed;
    (g) optionally removing traces of said at least one hardening solvent and thereby further hardening said first population of doxorubicin-loaded polymer microcapsules, nanocapsules, or mixtures thereof; and
    (h) removing said water soluble sublimable substance and said non-water soluble sublimable substance if present from doxorubicin-loaded population of polymer microcapsules, nanocapsules, or mixtures thereof to form echogenic doxorubicin-loaded polymer microcapsules, nanocapsules, or mixtures thereof which comprise at least 119% more of doxorubicin as compared to (1) echogenic doxorubicin-loaded polymer microcapsules, nanocapsules, or mixtures thereof prepared by adding doxorubicin prior to said emulsifying or (2) echogenic doxorubicin-loaded polymer microcapsules, nanocapsules, or mixtures thereof prepared by adding doxorubicin to lyophilized polymer microcapsules, nanocapsules, or mixtures thereof.

2. The method of claim 1, wherein step (e) further includes adding an extraction solvent and stirring to begin removal of the non-polar solvent.

3. The method of claim 1, wherein said removing of said water soluble sublimable substance and said non-water soluble sublimable substance if present is achieved by freeze drying.

4. The method of claim 1, wherein said removing of said at least one hardening solvent in step (g) is done by washing said first population of doxorubicin-loaded polymer microcapsules, nanocapsules, or mixtures thereof with a fresh portion of said at least one hardening solvent optionally comprising doxorubicin followed by washing with water or buffer.

5. The method of claim 4, wherein doxorubicin is added to at least one fresh portion of hardening solvent in step (g).

6. The method of claim 1, wherein in step (a), said at least one non-water soluble sublimable substance is dissolved in said at least one volatile non-polar solvent.

7. The method of claim 6, wherein said removing of said water soluble sublimable substance and said non-water soluble sublimable substance is achieved by freeze drying.

8. The method of claim 6, wherein said removing of said at least one hardening solvent in step (g) is done by washing said first population of doxorubicin-loaded polymer microcapsules, nanocapsules, or mixtures thereof with said at least one hardening solvent followed by washing with water or buffer.

9. The method of claim 8, wherein said doxorubicin is added to said at least one hardening solvent in step (g).

10. A hardening stage adsorption method for producing echogenic doxorubicin-loaded polymer microcapsules, nanocapsules, or mixtures thereof, the method comprising:
    (a) forming a first mixture comprising a solution of poly (D,L-lactic acid) (PLA) in at least one volatile non-polar solvent and optionally at least one non-water soluble sublimable substance;
    (b) adding at least one polar solvent to said first mixture to form a pre-emulsion;
    (c) emulsifying the pre-emulsion to produce a first population of polymer microcapsules, nanocapsules, or mixtures thereof comprising PLA and said at least one non-water sublimable soluble substance;
    (d) mixing said first population of polymer microcapsules, nanocapsules, or mixtures thereof with a surfactant solution and homogenizing to break apart said first population of polymer microcapsules, nanocapsules, or mixtures thereof to form a second population of polymer microcapsules, nanocapsules, or mixtures thereof that are smaller in size than said first population;
    (e) hardening said second population of polymer microcapsules, nanocapsules, or mixtures thereof by contacting with at least one hardening solvent comprising doxorubicin dissolved or dispersed in said at least one hardening solvent to form a first population of doxorubicin-loaded polymer microcapsules, nanocapsules, or mixtures thereof in which at least 95% of the non-polar solvent is removed;
    (f) optionally removing traces of said hardening solvent and thereby further hardening said first population of doxorubicin-loaded microcapsules, nanocapsules, or mixtures thereof; and
    (g) optionally removing said non-water soluble sublimable substance from doxorubicin-loaded population of polymer microcapsules, nanocapsules, or mixtures thereof to form echogenic doxorubicin-loaded polymer microcapsules, nanocapsules, or mixtures thereof which comprise at least 119% more of said drug as compared to (1) echogenic doxorubicin-loaded polymer microcapsules, nanocapsules, or mixtures thereof prepared by adding doxorubicin prior to said emulsifying or (2) echogenic doxorubicin-loaded polymer microcapsules, nanocapsules, or mixtures thereof prepared by adding doxorubicin to lyophilized polymer microcapsules, nanocapsules, or mixtures thereof.

11. A method of making echogenic doxorubicin-loaded polymer microcapsules, nanocapsules, or mixtures thereof, wherein a portion of doxorubicin is added to a water phase, an oil phase or both during formation of a population of polymer microcapsules, nanocapsules, or mixtures thereof from (i) a water/oil/water emulsion or (ii) a water/oil emulsion in the presence of a surfactant, wherein said water phase, said oil phase or both comprise a sublimable substance and wherein said oil phase comprises poly (D,L-lactic acid) (PLA) and a solvent, and wherein at the time said portion of doxorubicin is being added said population of polymer microcapsules, nanocapsules, or mixtures thereof is not hardened by (1) removal of a solvent or (2) lyophilization, the improvement comprising:
 (a) hardening said population of microcapsules or nanocapsules by contacting with at least one hardening solvent comprising an additional portion of doxorubicin dissolved or dispersed in said at least one hardening solvent to form a first population of doxorubicin-loaded polymer microcapsules, nanocapsules, or mixtures thereof in which at least 95% of the non-polar solvent is removed;
 (b) optionally removing traces of said hardening solvent and thereby further hardening said first population of doxorubicin-loaded polymer microcapsules, nanocapsules, or mixtures thereof; and
 (c) removing said sublimable substance from doxorubicin-loaded population of polymer microcapsules, nanocapsules, or mixtures thereof to form echogenic doxorubicin-loaded polymer microcapsules, nanocapsules, or mixtures thereof which comprise at least 119% more of said drug as compared to (1) echogenic doxorubicin-loaded polymer microcapsules, nanocapsules, or mixtures thereof prepared by adding doxorubicin prior to said emulsifying or (2) echogenic doxorubicin-loaded polymer microcapsules, nanocapsules, or mixtures thereof prepared by adding doxorubicin to lyophilized polymer microcapsules, nanocapsules, or mixtures thereof.

12. A method of making echogenic doxorubicin-loaded polymer microcapsules, nanocapsules, or mixtures thereof, the method comprising
 (a) forming a population of polymer microcapsules, nanocapsules, or mixtures thereof from (i) a water/oil/water emulsion or (ii) a water/oil emulsion in the presence of a surfactant, wherein said water phase, said oil phase or both comprise a sublimable substance and wherein said oil phase comprises poly (D, L-lactic acid) (PLA) and a solvent for said polymer, wherein a portion of doxorubicin is not added to said water phase, said oil phase or both during said forming of said population of polymer microcapsules, nanocapsules, or mixtures thereof and wherein said population of polymer microcapsules, nanocapsules, or mixtures thereof is dispersed in said solvent;
 (b) hardening said population of polymer microcapsules, nanocapsules, or mixtures thereof by contacting with at least one hardening solvent comprising doxorubicin dissolved or dispersed in said at least one hardening solvent to form a first population of doxorubicin-loaded polymer microcapsules, nanocapsules, or mixtures thereof in which at least 95% of the non-polar solvent is removed;
 (c) optionally removing traces of said hardening solvent and thereby further hardening said first population of doxorubicin-loaded polymer microcapsules, nanocapsules, or mixtures thereof; and
 (d) removing said sublimable substance from doxorubicin-loaded population of polymer microcapsules, nanocapsules, or mixtures thereof to form echogenic doxorubicin-loaded polymer microcapsules, nanocapsules, or mixtures thereof which comprise at least 119% more of doxorubicin as compared to (1) echogenic doxorubicin-loaded polymer microcapsules, nanocapsules, or mixtures thereof prepared by adding doxorubicin prior to said hardening or (2) echogenic doxorubicin-loaded polymer microcapsules, nanocapsules, or mixtures thereof prepared by adding doxorubicin to lyophilized polymer microcapsules, nanocapsules, or mixtures thereof.

13. Echogenic doxorubicin-loaded polymer microcapsules, nanocapsules, or mixtures thereof produced by the following steps:
 (a) forming a first mixture comprising a solution of poly (D, L-lactic acid) (PLA) in at least one volatile non-polar solvent and optionally at least one non-water soluble sublimable substance;
 (b) forming a second mixture comprising a solution of at least one water soluble sublimable substance in at least one polar solvent;
 (c) adding said first mixture to said second mixture to form a third mixture;
 (d) emulsifying the third mixture to produce a first population of polymer microcapsules, nanocapsules, or mixtures thereof comprising PLA, said at least one water-soluble sublimable substance, and optionally, said at least one non-water sublimable soluble substance;
 (e) mixing said first population of polymer microcapsules, nanocapsules, or mixtures thereof with a surfactant solution and homogenizing to break apart said first population of microcapsules or nanocapsules to form a second population of polymer microcapsules, nanocapsules, or mixtures thereof that are smaller in size than said first population;
 (f) hardening said second population of polymer microcapsules, nanocapsules, or mixtures thereof by contacting with at least one hardening solvent comprising doxorubicin dissolved or dispersed in said at least one hardening solvent to form a first population of doxorubicin-loaded polymer microcapsules, nanocapsules, or mixtures thereof in which at least 95% of the non-polar solvent is removed;
 (g) optionally removing traces of said at least one hardening solvent and thereby further hardening said first population of doxorubicin-loaded polymer microcapsules, nanocapsules, or mixtures thereof; and
 (h) removing said water soluble sublimable substance and said non-water soluble sublimable substance if present from doxorubicin-loaded population of polymer microcapsules, nanocapsules, or mixtures thereof to form echogenic doxorubicin-loaded polymer microcapsules, nanocapsules, or mixtures thereof;
 wherein said echogenic doxorubicin-loaded polymer microcapsules, nanocapsules, or mixtures thereof comprise at least 119% more of doxorubicin as compared to (1) echogenic doxorubicin-loaded polymer microcapsules, nanocapsules, or mixtures thereof prepared by adding doxorubicin prior to said emulsifying or (2) echogenic doxorubicin-loaded polymer microcapsules, nanocapsules, or mixtures thereof prepared by adding doxorubicin to lyophilized polymer microcapsules, nanocapsules, or mixtures thereof.

* * * * *